United States Patent [19]

Shu et al.

[11] Patent Number: 5,994,543
[45] Date of Patent: Nov. 30, 1999

[54] ANTIBIOTIC BRAVOMICINS

[75] Inventors: Yue-Zhong Shu; Jie Chen, both of Cheshire; Kin Sing Lam, North Haven; Judith A. Veitch, Wallingford; Daniel Brown, Killingworth, all of Conn.

[73] Assignee: Bristol-Myers Squibb Company, Princeton, N.J.

[21] Appl. No.: 09/262,693

[22] Filed: Mar. 4, 1999

Related U.S. Application Data

[60] Provisional application No. 60/078,745, Mar. 20, 1998, abandoned.

[51] Int. Cl.$^6$ ...................... C07D 403/00; C07D 241/04; A01N 43/60
[52] U.S. Cl. ...................... 544/359; 544/380; 544/383; 544/385; 514/255
[58] Field of Search ...................... 544/359, 380, 544/383, 385; 514/255

[56] References Cited

U.S. PATENT DOCUMENTS 4,307,085 12/1981 Waitz et al. ............................ 424/181

OTHER PUBLICATIONS

M. L. Cohen "Antimicrobial Resistance: Prognosis for Public Health," Trends in Microbiology, 2, pp. 422–425, 1994.

*Primary Examiner*—Mukund J. Shah
*Assistant Examiner*—Tamthom N. Truong
*Attorney, Agent, or Firm*—David M. Morse

[57] ABSTRACT

A novel class of antibiotics, designated bravomicins, is obtained by fermentation of a strain of *Micromonospora polytrota*. Six bioactive compounds, designated bravomicins A, B, C, D, E and F, are obtained and found to be useful in the treatment of a wide variety of bacterial diseases.

10 Claims, 9 Drawing Sheets

000
ANTIBIOTIC BRAVOMICINS

CROSS-REFERENCE TO RELATED APPLICATION

This application claims the benefit of U.S. provisional application Ser. No. 60/078,745 filed Mar. 20, 1998, now abandoned.

BACKGROUND OF THE INVENTION

1. Field of the Invention

This invention relates to a novel class of antibiotics, designated by the present inventors as bravomicins, which may be obtained by cultivation of a strain of *Micromonospora polytrota*. The present invention also provides O- and N-acylated derivatives of the novel bravomicins. The compounds of the present invention are useful in the treatment of bacterial diseases.

2. Background Art

Emergence of bacterial resistance to a number of antimicrobial agents such as beta-lactam antibiotics, macrolides, quinolones, and vancomycin is becoming a major worldwide health problem. (Cohen, M. L. Antimicrobial resistance: prognosis for public health. *Trends Microbiol.* 1994, 2, 422–425). The most significant problem in clinical practice is the increase in the isolation of methicillin-resistant *Staphylococcus aureus* (MRSA) strains. In the United States, by the early 1990s MRSA was detected in 20–40% of all *S. aureus* hospital isolates reported to the National Nosocomial Infections Surveillance (NNIS) System and is also a major problem in long-term care facilities. Other than the United States, the occurrence of epidemic strains of MRSA has also been reported in many countries such as Argentina, Australia, Belgium, Canada, Denmark, France, Germany, Greece, Hong Kong, Italy, Japan Malaysia, Netherlands, New Zealand, Portugal, Spain, Sweden, Taiwan, and the United Kingdom. In addition to resistance to beta-lactam antibiotics, multiply resistant MRSA are also resistant to macrolides, tetracyclines, aminoglycosides, and fluoroquinolones. At present, the only effective treatment for multiply resistant MRSA infections is vancomycin. However, the minimum inhibitory concentration (MIC) for vancomycin against some MRSA isolates has been increasing recently, leading to a situation where standard doses of vancomycin may not be effective for severe infections. (Major Unmet Needs in Bacterial Infection Therapy. Infectious Disease, A Pharmacor Service, August, 1992.)

Enterococci are another group of bacteria which are generally resistant to antibiotics such as penicillins, cephalosporins, and aminoglycosides. Current treatment for enterococcal infection is the use either of a combination of two antibiotics or of vancomycin alone. However, with the recent increased use of vancomycin in MRSA infections and colitis due to *Clostridium difficile*, multiply resistant *Enterococcus faecium* has emerged. In a recent report to the Center of Disease Control's NNIS, the percentage of nosocomial enterococci resistant to vancomycin increased from 0.3% in 1989 to 7.9% in 1993. Because of the fact that only a few drugs can be used effectively to treat enterococcal infections, treatment options for patients infected with vancomycin-resistant enterococci are very limited. Furthermore, the Gram-negative organisms such as Pseudomonas, Klebsiella, Proteus, and Enterobacter species were the important antibiotic resistant pathogens in the 1970s; they remain a highly risky problem in some hospitals today.

Apart from the nosocomial pathogens described above, the resistance of the important community-acquired pathogen *Streptococcus pneumoniae* to penicillin and other antibacterials is becoming a worldwide problem. Multidrug-resistant strains of *Mycobacterium tuberculosis* have emerged in several countries including the United States. The emergence and spread of resistant nosocomial and community-acquired pathogens is generating a great threat to public health worldwide. There is an urgent need to discover new agents to treat patients infected with these multidrug-resistant bacteria.

The present invention provides what appears to be a new class of antibiotics. They were produced by fermentation of a strain of *Micromonospora polytrota* previously disclosed in U.S. Pat. No. 4,307,085 as being used to prepare a different class of antibiotics described as the AR-5 antibiotic complex.

SUMMARY OF THE INVENTION

Figure 1:
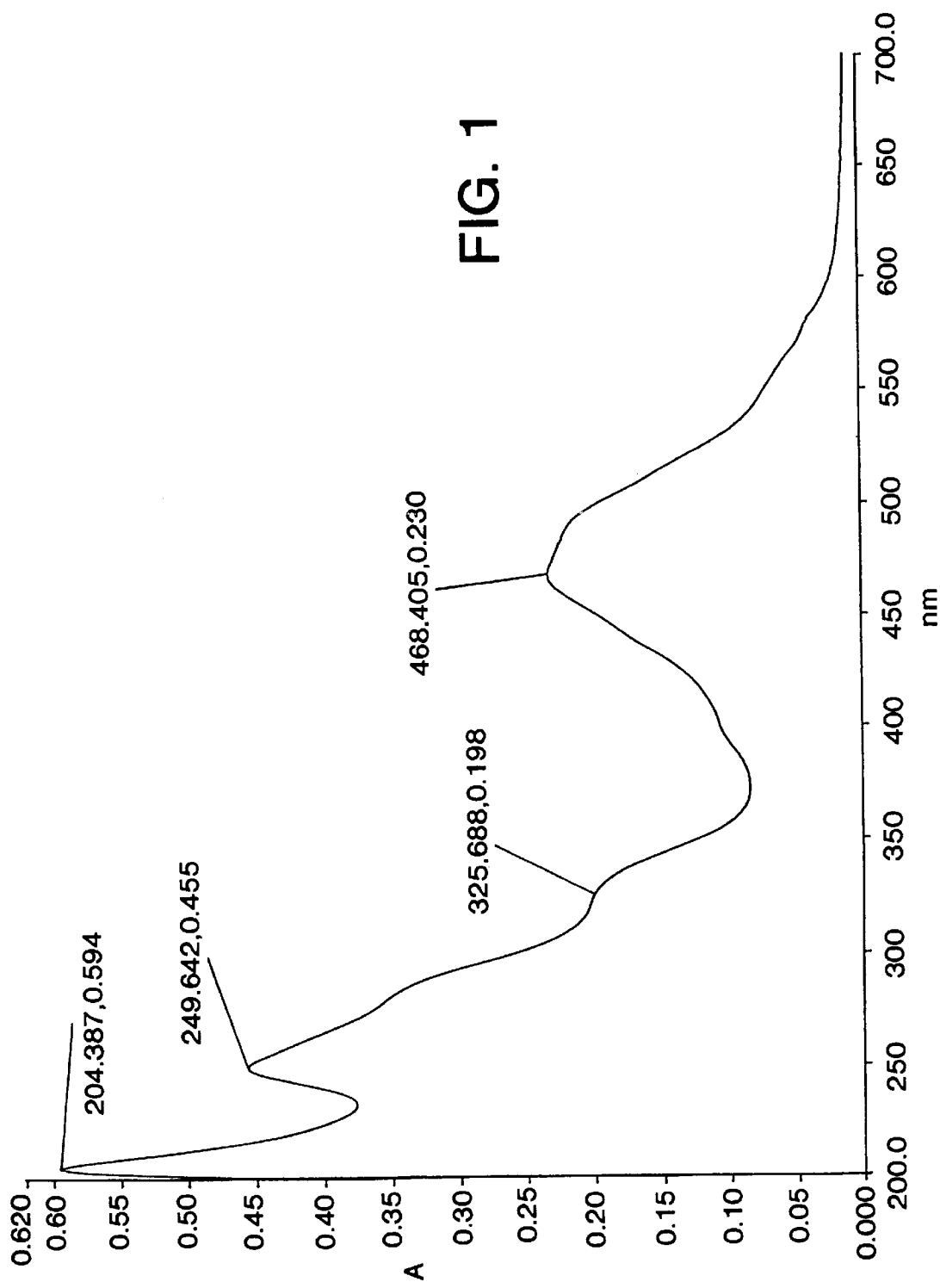
FIG. 1 shows the ultraviolet absorption spectrum of bravomicin A in methanol.

The present invention provides a novel complex of antibacterial antibiotics, designated by the present inventors as bravomicins. Six naturally-occuring members of the bravomicin class have been obtained and isolated, designated herein as bravomicin A, B, C, D, E and F. Additionally, acylation products of these natural products have been produced by O-acylation and N-acylation as described herein. The bravomicin compounds provided by the present invention are potent antibacterial agents.

Also provided by the present invention are pharmaceutical compositions of the bravomicins, methods for the treatment of bacterial infections and processes for producing the natural bravomicins and acylation products.

DETAILED DESCRIPTION OF THE INVENTION

U.S. Pat. No. 4,307,085 describes the fermentation of *Micromonospora polytrota* ATCC-31584 to produce an antibiotic complex designated as AR-5. The present inventors unexpectedly discovered that the fermentation broth produced by cultivating *Micromonospora polytrota* ATCC-31584 also produces a novel antibiotic complex not reported in the above-mentioned patent or in other literature. This complex, designated by the present inventors as bravomicin, is provided by the present invention along with certain acylation products of the naturally occuring antibiotics.

The producing microorganism used to obtain the naturally occuring bravomicin antibiotics of the present invention is the same *Micromonospora polytrota* identified in U.S. Pat. No. 4,307,085 as being deposited under accession number ATCC-31584. To assure compliance with the Budapest Treaty, the present inventors have deposited another sample of this producing organism with the American Type Culture Collection (ATCC), Rockville, Md., USA, under accession number ATCC-202091. In addition to the specific deposited microorganism, it should be understood that bravomicin-producing mutants such as those produced by the use of chemical or physical mutagens including X-rays, etc. and organisms whose genetic makeup has been modified by molecular biology techniques may also be cultivated to produce bravomicins.

The production of bravomicin complex (as used herein, "bravomicin complex" is intended to mean a mixture of bravomicins A, B, C, D, E and F) may be carried out by cultivating a bravomicin-producing strain of *Micromonospora polytrota*, preferably a strain having the identifying characteristics of ATCC-202091, or a bravomicin-producing mutant thereof, in a suitable aqueous nutrient medium containing assimilable sources of carbon and nitrogen under submerged aerobic conditions until a substantial amount of bravomicin complex is produced in the fermentation broth (as determined by assay techniques described below), and then recovering the desired bravomicin A, B, C, D, E and/or F from the fermentation broth, preferably in substantially pure form free of co-produced substances. The bravomicin complex may be harvested from the mycelial growth with a suitable solvent, the solution containing the desired component concentrated and the concentrated material then subjected to chromatographic separation to purify the component.

The sources of assimilable carbon include glucose, fructose, mannose, maltose, galactose, mannitol and glycerol, other sugars and sugar alcohols, starches and other carbohydrates, or carbohydrate derivatives such as dextran or cerelose, as well as complex nutrients such as oat flour, corn meal, millet, corn and the like. The exact quantity of the carbon source which is utilized in the medium will depend in part, upon the other ingredients in the medium, but it is usually found that an amount of carbohydrate between 0.5 to 10 percent by weight of the medium is satisfactory. These carbon sources can be used individually or several such carbon sources may be combined in the same medium.

The sources of assimilable nitrogen include amino acids such as glycine, arginine, threonine, methionine and the like, ammonium salts, as well as complex sources such as yeast extracts, corn steep liquors, distiller solubles, soybean meal, cotton seed meal, fish meal, and the like. The various sources of nitrogen can be used alone or in combination in amounts ranging from 0.05 to 5 percent by weight of the medium.

Nutrient inorganic salts may also be incorporated in the culture medium, if desired. Suitable are the customary salts capable of yielding sodium, potassium, magnesium, calcium, phosphate, sulfate, chloride, carbonate, and like ions. Also included are trace metals such as cobalt, magnesium, iron, molybdenum, zinc, cadmium, and the like.

The progress of fermentation and the isolation procedure may be monitored by means of an antibacterial broth dilution assay against a multiply drug resistant *Enterococcus faecium* strain. A more detailed description of a suitable assay procedure is found below. In the case of column chromatography, an aliquot of column fractions was transferred by a liquid handler to a corresponding well in a 96 well microtiter plate, the plate was dried, and submitted to the broth dilution assay against the test strain. In the case of thin layer chromatography (TLC), active spots on the plate were detected by means of bioautography in an agar diffusion assay against the same test strain.

Bravomicins may be isolated and purified from the fermentation broth by means of art-recognized techniques. The mycelia of *Micromonospora polytrota* fermentation may be obtained by centrifugation, the mycelia extracted with a solvent mixture of methanol and chloroform, and this mixture then concentrated in vacuo to a residue. The residue is subjected to repeated solvent partitioning. Further separation is effected by Sephadex LH-20 chromatography, and medium pressure reversed phase liquid chromatography. These steps yield a complex of compounds having activity in the antibacterial assay. Final purification of bravomicins may be accomplished by preparative HPLC.

The bravomicins exist as a complex of six component antibiotics designated as bravomicins A, B, C, D, E and F. These six components exist in a conformational equilibrium between two rotameric forms as shown below:

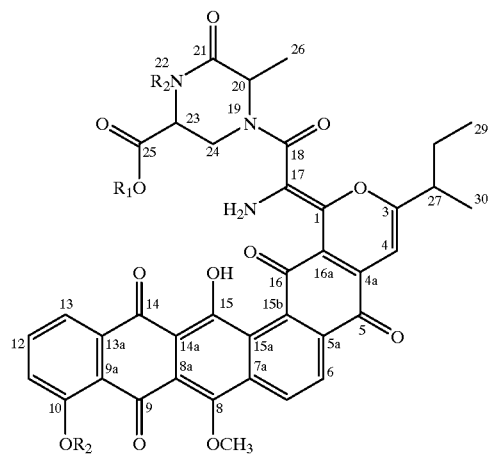

Bravomicin A: $R_1 = R_2 = H$
Bravomicin A diacetate: $R_1 = H, R_2 = COCH_3$
Bravomicin B: $R_1 = CH_3, R_2 = H$
Bravomicin C: $R_1 = CH_2CH_3, R_2 = H$

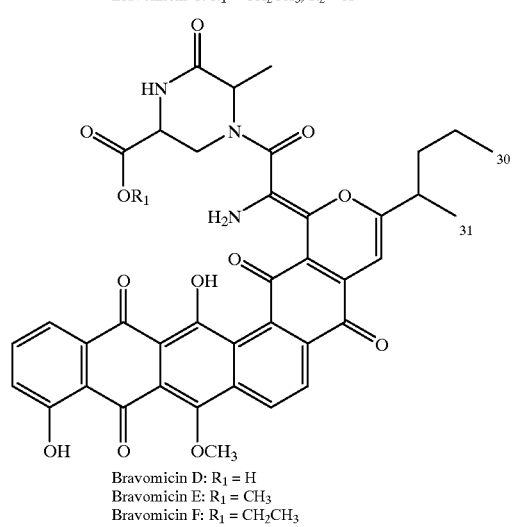

Figure 2:
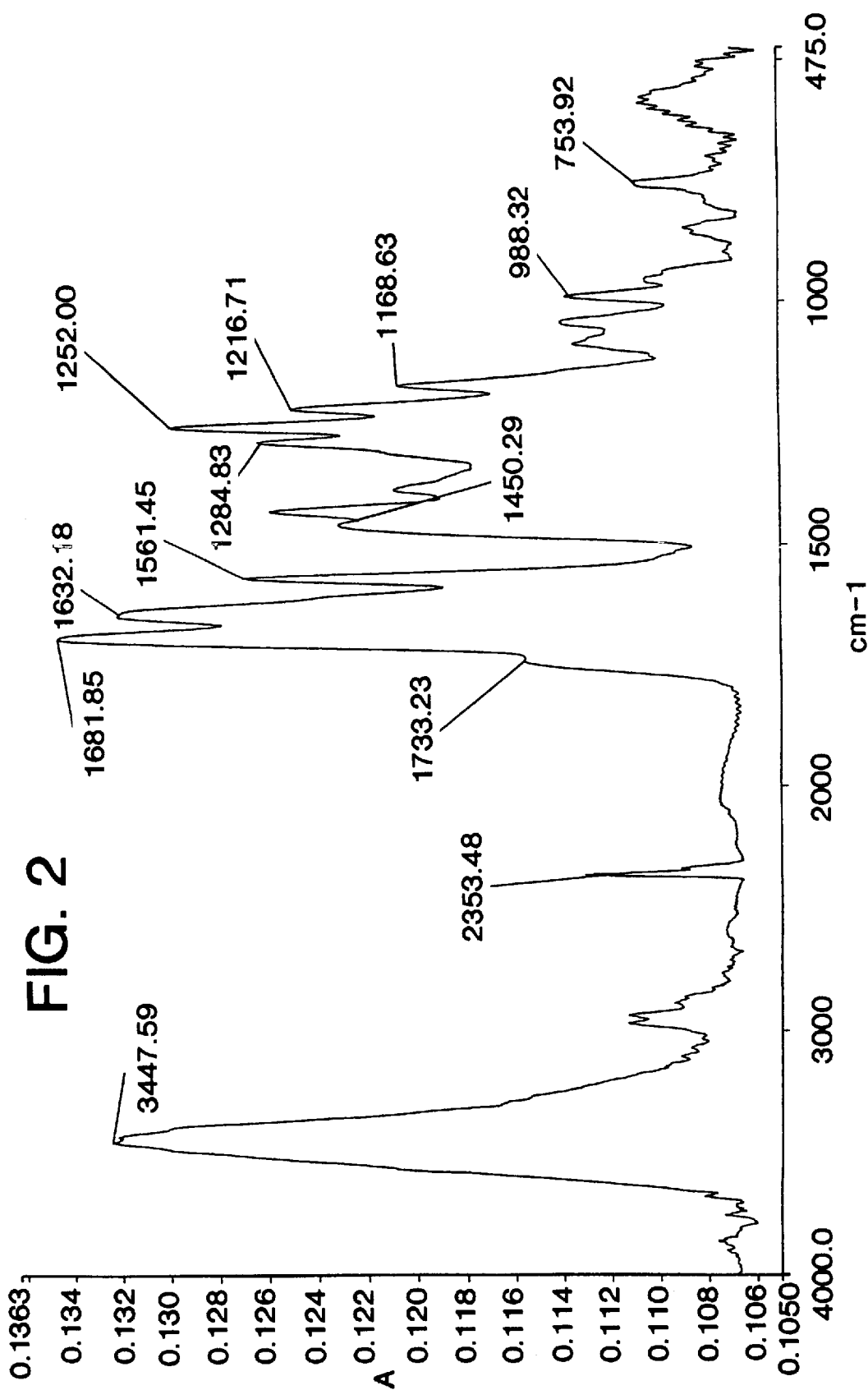
FIG. 2 shows the infrared absorption spectrum of bravomicin A (KBr pellet).
Figure 3:
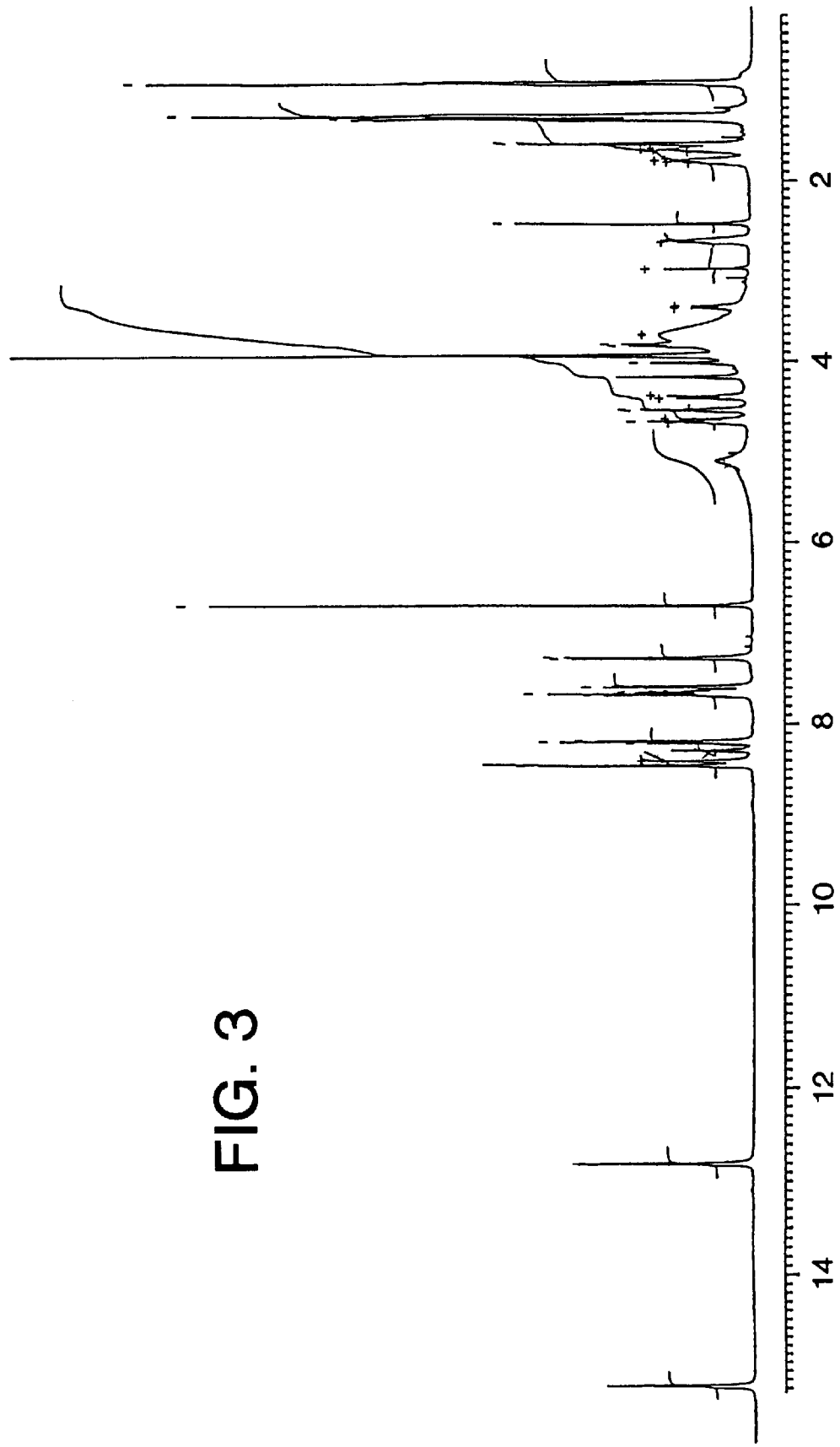
FIG. 3 shows the proton magnetic resonance spectrum of bravomicin A in DMSO-$d_6$.
Figure 4:
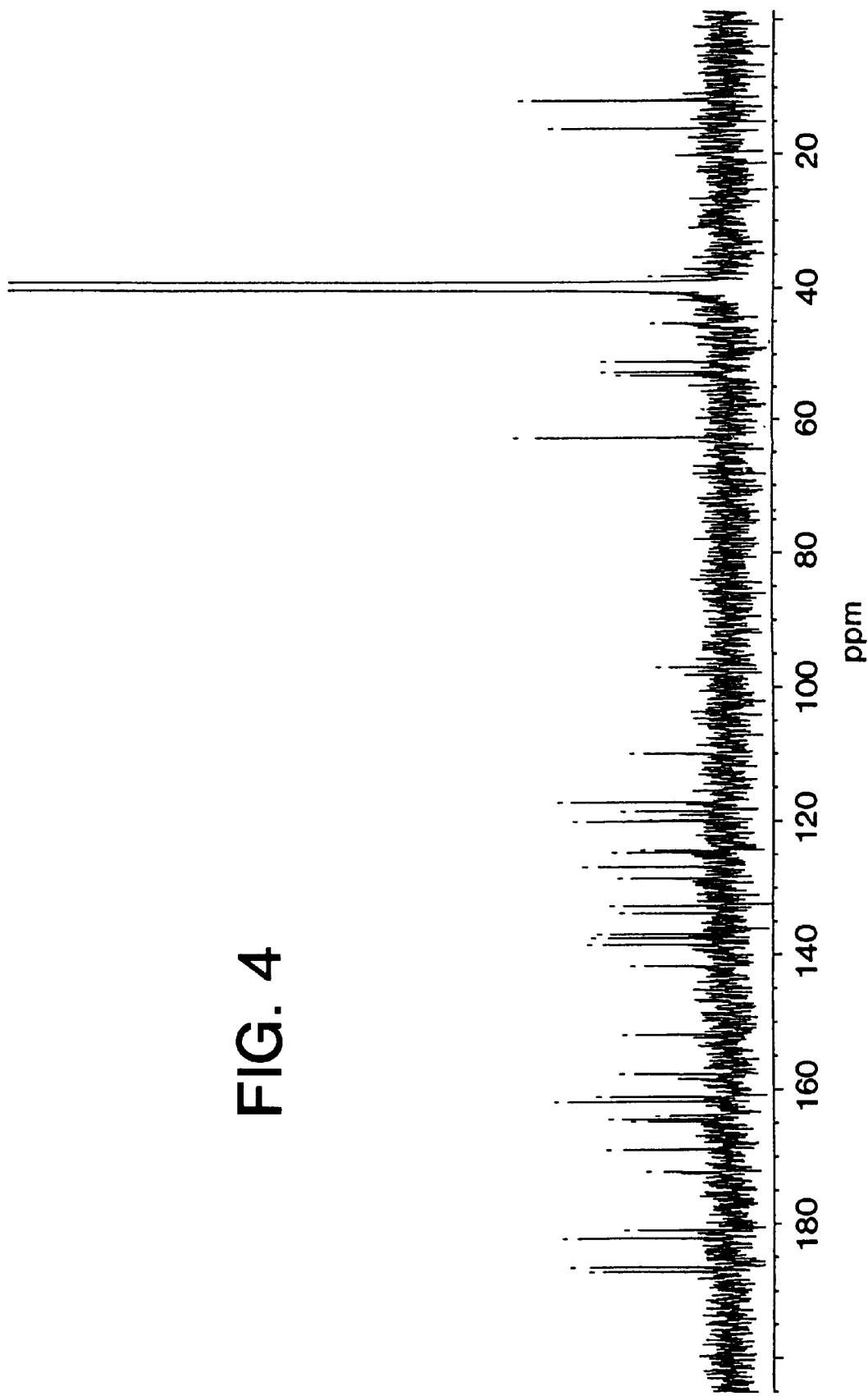
FIG. 4 shows the carbon-13 magnetic resonance spectrum of bravomicin A in DMSO-$d_6$.

Bravomicin D: $R_1 = H$
Bravomicin E: $R_1 = CH_3$
Bravomicin F: $R_1 = CH_2CH_3$ Bravomicin A, the major compound in the bravomicin class, is a reddish orange amorphous powder. It is soluble in dimethyl sulfoxide and the solvent mixture of chloroform/methanol (1:1), partially soluble in methanol, acetone, acetonitrile and chloroform, but insoluble in hexane. The compound has been found to be an inseparable rotameric mixture(60%: 40%) as shown in the Scheme below and has the following characteristics: mp. 208–210° C. $[\alpha]_D$ –25.4° (c0.66, MeOH/CHCl$_3$, 1:1); UV (MeOH)λ max (log ε) 250 (4.46), 281 (sh., 4.32), 326 (4.10), 468 (4.17) nm (FIG. 1); IR (KBr) ν max 3447, 2961, 1733, 1681, 1632, 1561, 1450, 1410, 1284, 1252, 1216, 1168, 988, 753 cm$^{-1}$ (FIG. 2) HRFABMS: found 720.1850, calcd. for (M–H)$^-$, C$_{38}$H$_{30}$N$_3$O$_{12}$ 720.1878; Molecular weight, 721.68. Positive electrospray MS (relative intensity %) m/z: 744 (9, [M+Na]$^+$), 722 (11, [M+H]$^+$); Negative electrospray MS (relative intensity %) m/z: 720 (100, [M–H]$^-$); $^1$H-NMR spectrum (500 MHz) in DMSO-d$_6$ in Table 1 and FIG. 3. $^{13}$C-NMR spectrum (125 MHz) in DMSO-d$_6$ in Table 2 and FIG. 4.

Figure 6:
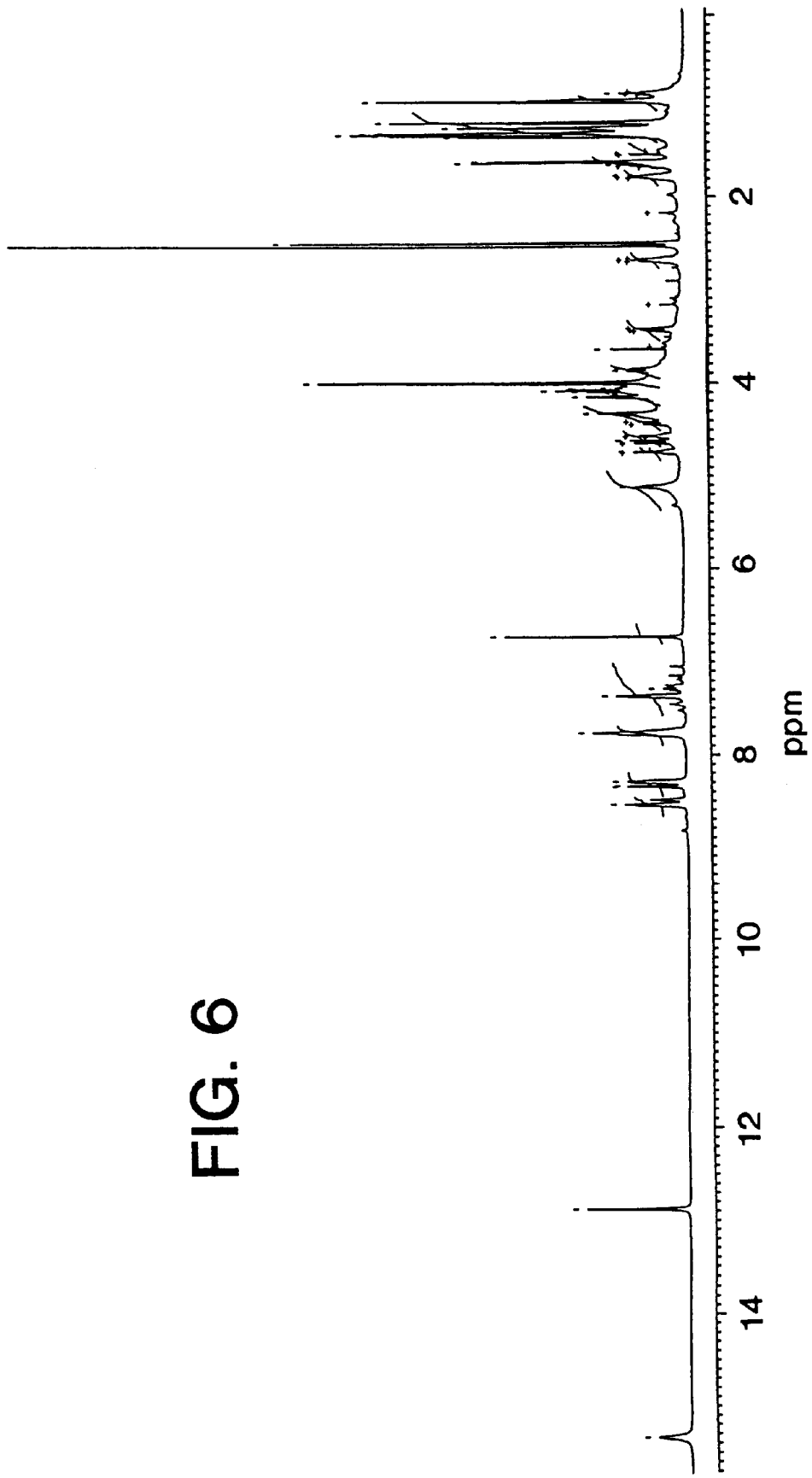
FIG. 6 shows the proton magnetic resonance spectrum of bravomicin C in DMSO-$d_6$.

Table 1 and FIG. 6. $^{13}$C-NMR spectrum (125 MHz) in DMSO-d$_6$ in Table 2.

Bravomicin D, a reddish orange amorphous powder, is soluble in dimethyl sulfoxide and the solvent mixture of chloroform/methanol (1:1), partially soluble in methanol, acetone, acetonitrile and chloroform, but insoluble in hexane. The compound has been found to be an inseparable rotamiieric mixture (60%: 40%) and has the following characteristics: molecular formula C$_{39}$H$_{33}$N$_3$O$_{12}$; molecular weight, 735.71; UV (MeOH) λ max (log ε) 250 (4.49), 281 (sh., 4.31), 326 (4.02), 468 (4.17) nm; Positive electrospray MS (relative intensity %) m/z: 758 (100, [M+Na]$^+$), 736 (92, [M+H]$^+$), 529 (35), 507 (42); Negative electrospray MS (relative intensity %) m/z: 734 (57, [M–H]$^-$), 367 (100);

Scheme: Rotameric mixture of bravomicin

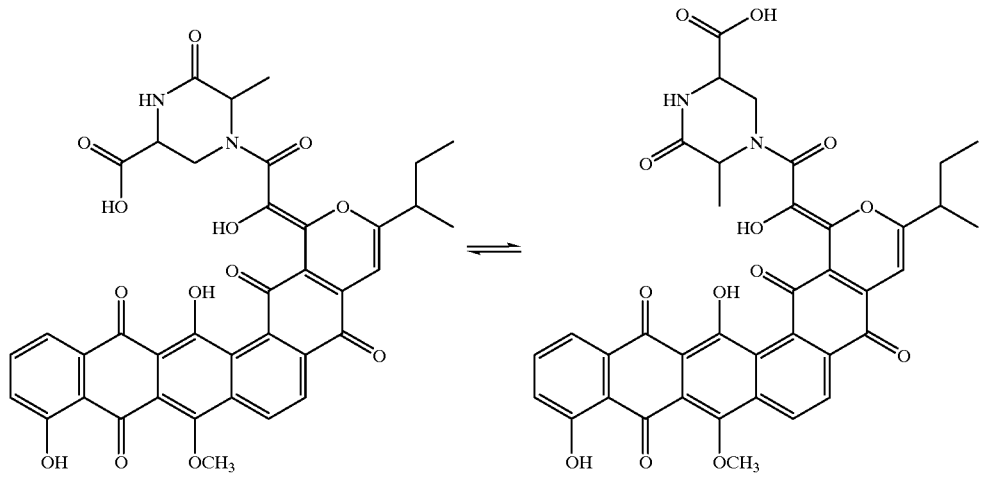

Figure 5:
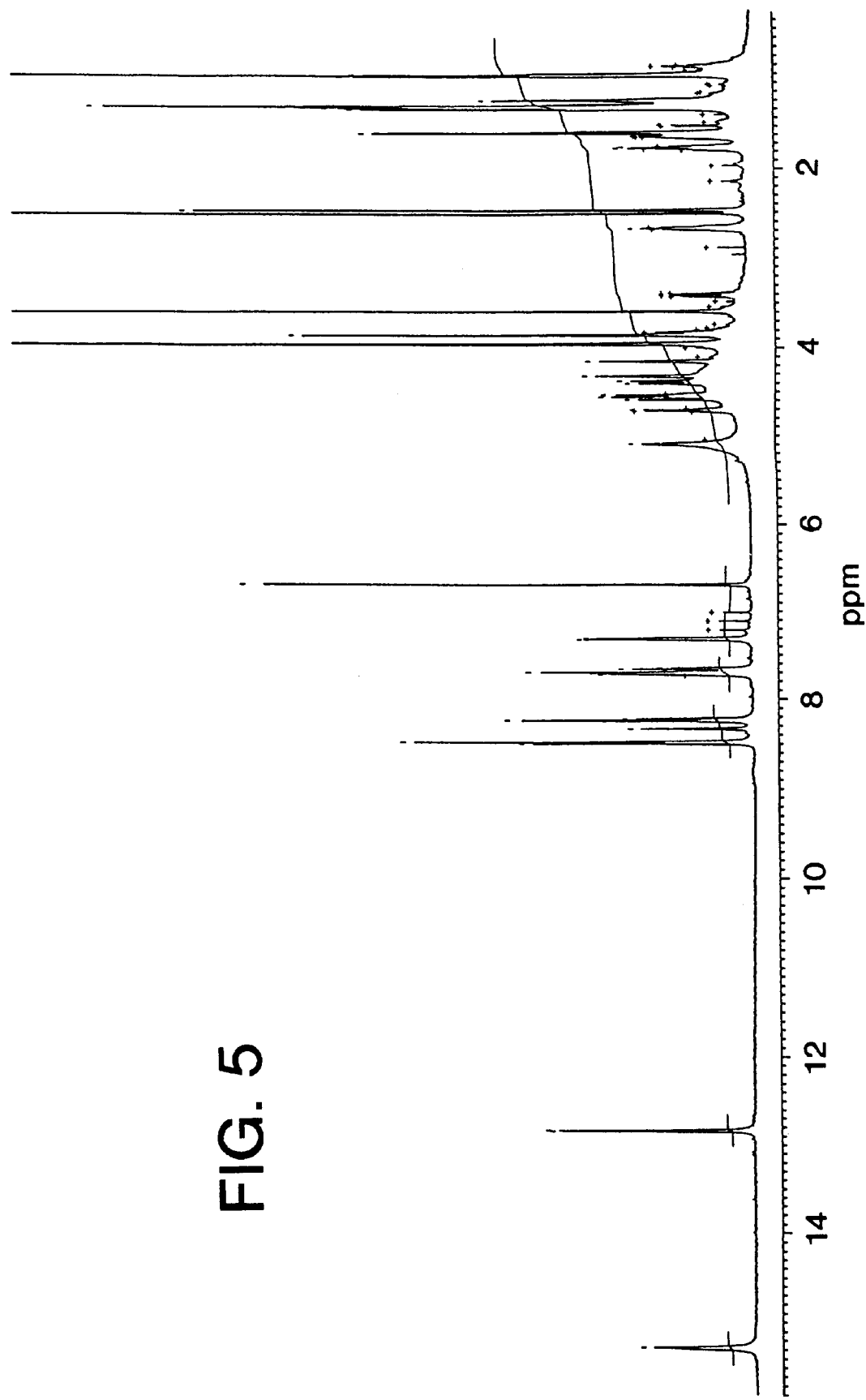
FIG. 5 shows the proton magnetic resonance spectrum of bravomicin B in DMSO-$d_6$.

Bravomicin B, a reddish orange amorphous powder, is soluble in dimethyl sulfoxide and the solvent mixture of chloroform/methanol (1:1), partially soluble in methanol, acetone, acetonitrile and chloroform, but insoluble in hexane. The compound has been found to be an inseparable rotameric mixture (55%: 45%) and has the following characteristics: molecular formula C$_{39}$H$_{33}$N$_3$O$_{12}$; molecular weight, 735.71; UV (MeOH) λ max (log ε) 249 (4.43), 281 (sh., 4.27), 325 (4.00), 467 (4.14) nm; IR (KBr) ν max 3432, 2997, 1735, 1676, 1638, 1561, 1458, 14223, 1284, 1253, 1205, 1166, 1135, 1046, 988, 753 cm$^{-1}$; Positive electrospray MS (relative intensity %) m/z: 758 (12, [M+Na]$^+$), 736 (45, [M+H]$^+$); Negative electrospray MS (relative intensity %) m/z: 734 (42, [M–H]$^-$); $^1$H-NMR spectrum (500 MHz) in DMSO-d$_6$ in Table 1 and FIG. 5. $^{13}$C-NMR spectrum (125 MHz) in DMSO-d$_6$ in Table 2.

Figure 7:
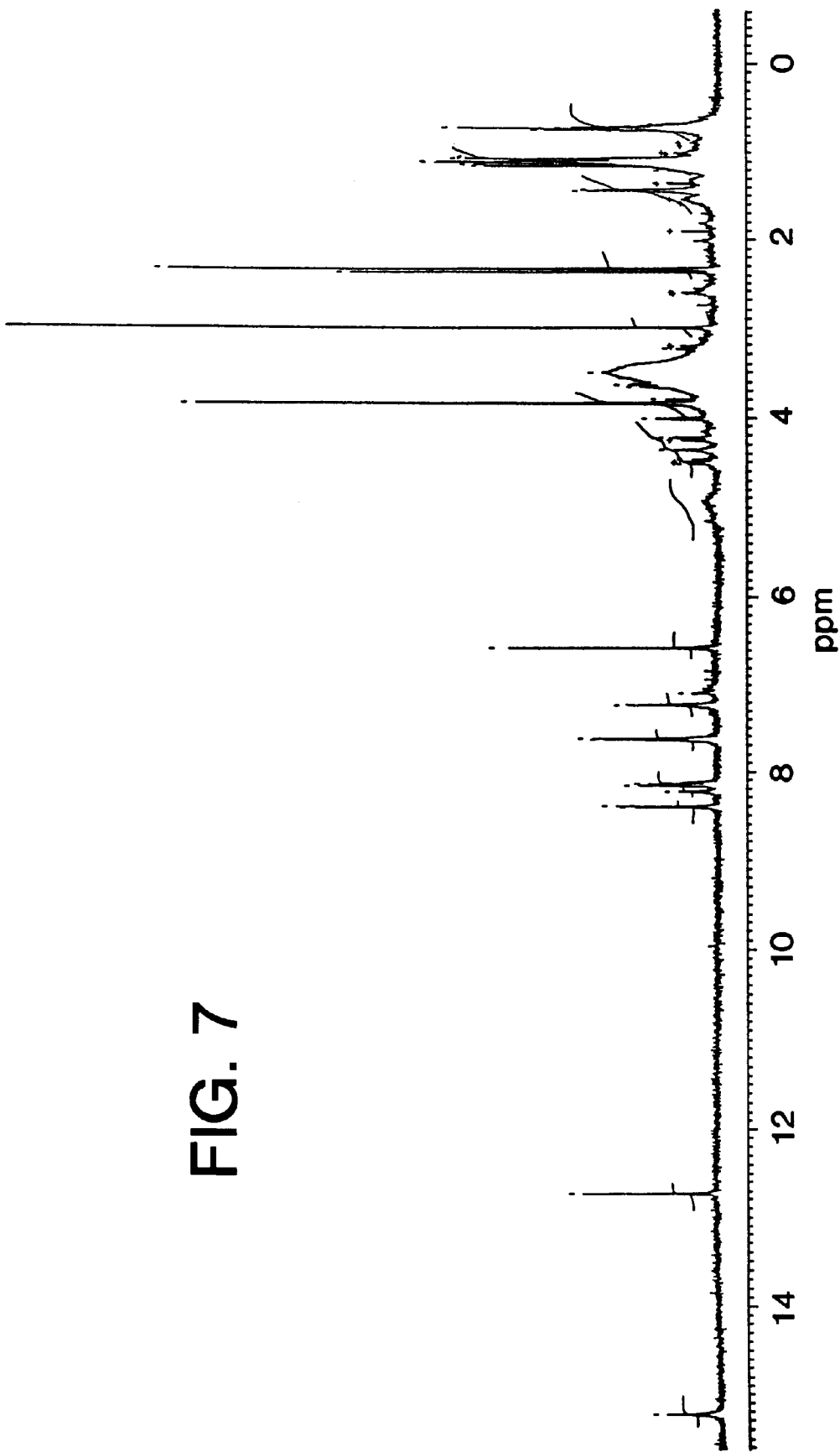
FIG. 7 shows the proton magnetic resonance spectrum of bravomicin D in DMSO-$d_6$.

Bravomicin C, a reddish orange amorphous powder, is soluble in dimethyl sulfoxide and the solvent mixture of chloroform/methanol (1:1), partially soluble in methanol, acetone, acetonitrile and chloroform, but insoluble in hexane. The compound has been found to be an inseparable rotameric mixture (50%: 50%) and has the following characteristics: molecular formula C$_{40}$H$_{35}$N$_3$O$_{12}$; molecular weight, 749.74; UV (MeCOH) λ max (log ε) 250 (4.44), 281 (sh., 4.26), 325 (4.03), 467 (4.18) nm; Positive electrospray MS (relative intensity %) m/z: 750 (28, [M+H]$^+$); Negative electrospray MS (relative intensity %) m/z: 748 (47, [M–H]$^-$); $^1$H-NMR spectrum (500 MHz) in DMSO-d$_6$ in $^1$H-NMR spectrum (500 MHz) in DMSO-d$_6$ in Table 1 and FIG. 7. $^{13}$C-NMR spectrum (125 MHz) in DMSO-d$_6$ in Table 2.

Figure 8:
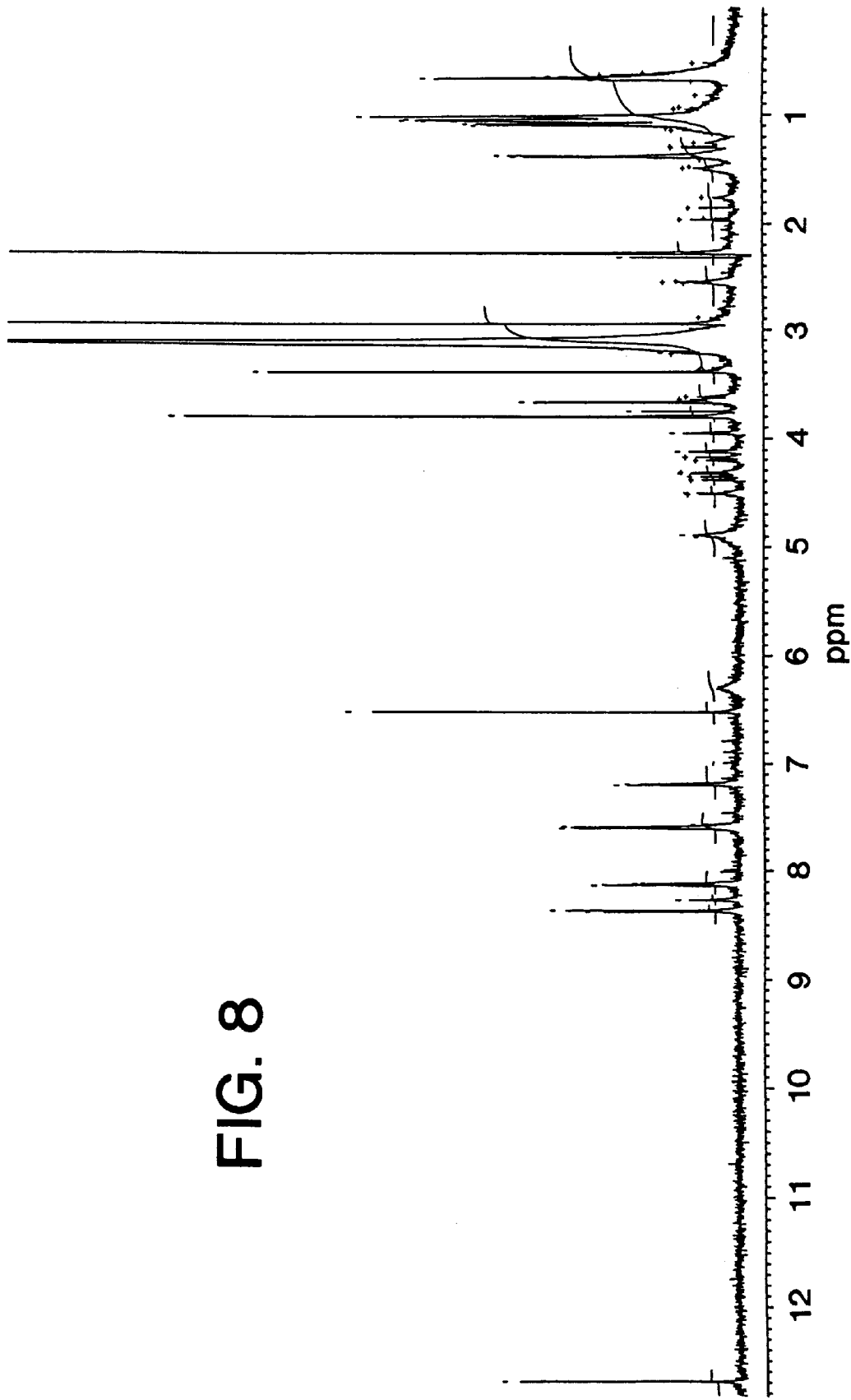
FIG. 8 shows the proton magnetic resonance spectrum of bravomicin E in DMSO-$d_6$.

Bravomicin E, a reddish orange amorphous powder, is soluble in dimethyl sulfoxide and the solvent mixture of chloroform/methanol (1:1), partially soluble in methanol, acetone, acetonitrile and chloroform, but insoluble in hexane. The compound has been found to be an inseparable rotameric mixture (55%: 45%) and has the following characteristics: molecular formula C$_{40}$H$_{35}$N$_3$O$_{12}$; molecular weight, 749.74; UV (MeOH) λ max (log ε) 250 (4.52), 281 (sh., 4.32), 325 (4.03), 469 (4.18) nm; Positive electrospray MS (relative intensity %) m/z: 772 (58, [M+Na]$^+$), 750 (100, [M+H]$^{30}$ ); Negative electrospray MS (relative intensity %) m/z: 748 (100, [M–H]$^-$); $^1$H-NMR spectrum (500 MHz) in DMSO-d$_6$ in Table 1 and FIG. 8. $^{13}$C-NMR spectrum (125 MHz) in DMSO-d$_6$ in Table 2.

Bravomicin F, a reddish orange amorphous powder, is soluble in dimethyl sulfoxide and the solvent mixture of chloroform/methanol (1:1), partially soluble in methanol, acetone, acetonitrile and chloroform, but insoluble in hexane. The compound has been found to be an inseparable rotameric mixture (50%: 50%) and has the following characteristics: molecular formula C$_4$H$_{37}$N$_3$O$_{12}$; molecular weight, 763.76; UV (MeOH) λ max (log ε) 249 (4.56), 280 (sh., 4.28), 326 (4.06), 468 (4.14) nm; Positive electrospray MS (relative intensity %) m/z: 786 (88, [M+Na]$^+$), 764 (100, [M+H]$^+$); Negative electrospray MS (relative intensity %) m/z: 762 (46, [M–H]$^-$), 281 (37); $^1$H-NMR spectrum (500

Figure 9:
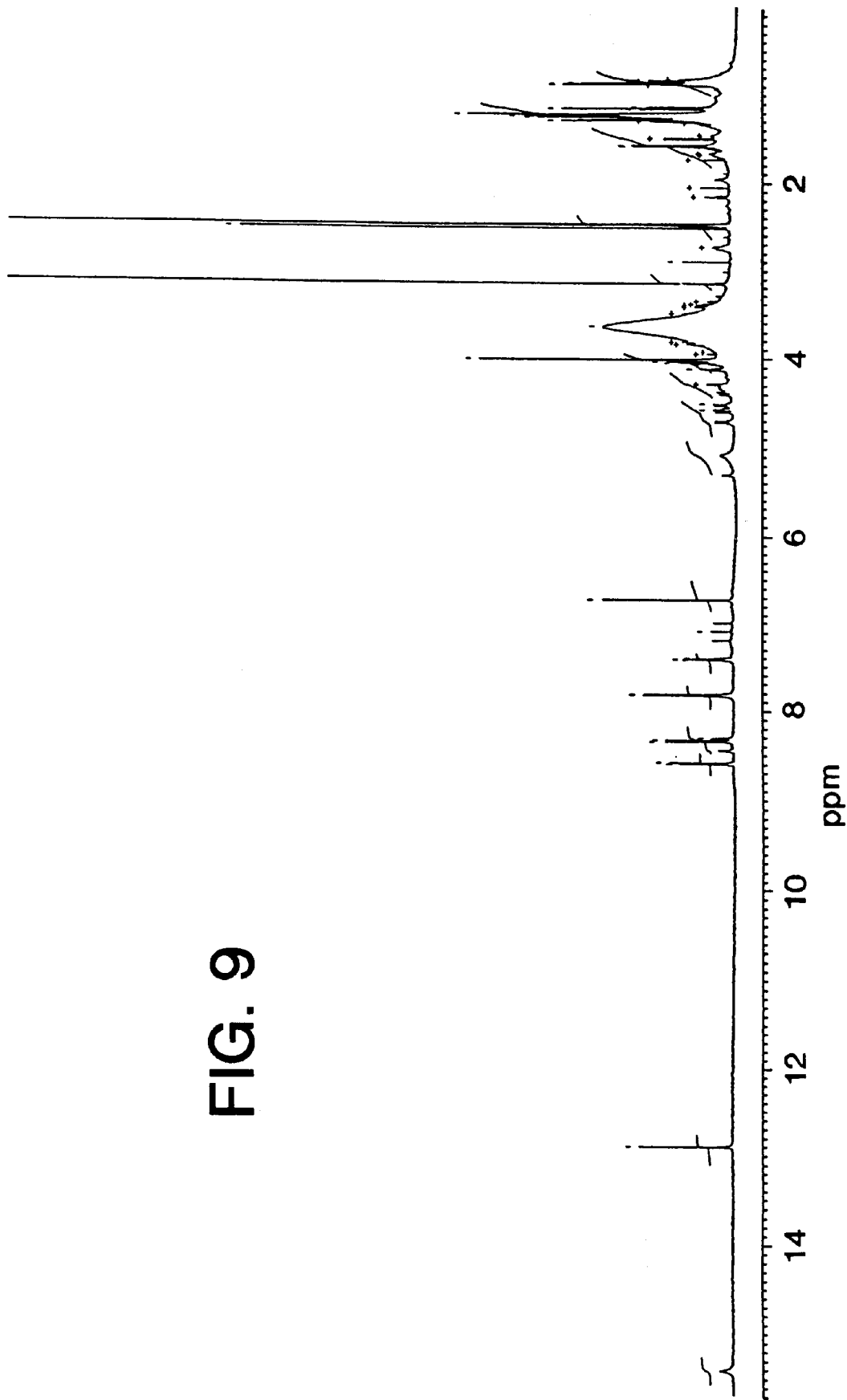
FIG. 9 shows the proton magnetic resonance spectrum of bravomicin F in DMSO-$d_6$.

MHz) in DMSO-$d_6$ in Table 1 and FIG. 9. $^{13}$C-NMR spectrum (125 MHz) in DMSO-$d_6$ in Table 2.

TABLE 1

$^1$H-NMR data of bravomicins

Bravomicin A

| $^1$H-Position | Rotamer A (60%) | Rotamer B (40%) |
|---|---|---|
| 4 | 6.72(s) | 6.72(s) |
| 6 | 8.22(d, 8.6) | 8.22(d, 8.6) |
| 7 | 8.48(d, 8.6) | 8.48(d, 8.6) |
| 8-OMe | 3.97(s) | 3.97(s) |
| 10-OH | 12.83(s) | 12.83(s) |
| 11 | 7.29(dd, 8.1, 1.8) | 7.29(dd, 8.1, 1.8) |
| 12 | 7.69(m) | 7.69(m) |
| 13 | 7.64(m) | 7.64(m) |
| 15-OH | 15.38(s) | 15.38(s) |
| 17-NH2 | 5.10(br s) | 5.10(br s) |
| 20 | 4.58(q, 6.7) | 4.71(q, 6.7) |
| 22-NH | 8.43(br s) | 8.31(br d, 3.6) |
| 23 | 4.20(br s) | 4.04(br s) |
| 24 | 3.84(dd 14.1, 3.2), 4.41(d, 14.1) | 3.42(dd, 14.2, 3.2), 4.68 (d, 14.2) |
| 26 | 1.35(d, 6.7) | 1.61(d, 6.7) |
| 27 | 1.31(d, 6.3) | 1.31(d, 6.3) |
| 28 | 2.68(m) | 2.68(m) |
| 29 | 1.70(m), 1.8.1(m) | 1.70(m), 1.81(m) |
| 30 | 0.95(t, 7.1) | 0.95(t, 7.1) |

Bravomicin A diacetate

| $^1$H-Position | Rotamer A (60%) | Rotamer B (40%) |
|---|---|---|
| 4 | 6.60(s) | 6.60(s) |
| 6 | 8.18(d, 8.8) | 8.18(d, 8.8) |
| 7 | 8.42(d, 8.8) | 8.42(d, 8.8) |
| 8-OMe | 3.81(s) | 3.81(s) |
| 10-Ac | 2.31(s) | 2.31(s) |
| 11 | 7.52(br d, 7.6) | 7.52(br d, 7.6) |
| 12 | 7.80(m) | 7.80(m) |
| 13 | 8.08(m) | 8.08(m) |
| 15-OH | 14.84(s) | 14.84(s) |
| 17-NH2 | 5.04(br s) | 5.04(br s) |
| 20 | 4.64(q, 6.7) | 4.98(q, 6.7) |
| 22-Ac | 2.41(s) | 2.41(s) |
| 23 | 4.89(br s) | 4.64(br s) |
| 24 | 3.85(dd, 14.1, 3.2), 4.42(d, 14.1) | 3.42(dd, 14.1, 3.2), 4.60 (d, 14.1) |
| 26 | 1.30(d, 6.7) | 1.59(d, 6.7) |
| 27 | 1.13(d, 6.3) | 1.13(d, 6.3) |
| 28 | 2.50(m) | 2.50(m) |
| 29 | 1.50(m), 1.60(m) | 1.50(m), 1.60(m) |
| 30 | 0.7(t, 7.1) | 0.7(t, 7.1) |

Bravomicin B

| $^1$H-Position | Rotamer A (55%) | Rotamer B (45%) |
|---|---|---|
| 4 | 6.71(s) | 6.71(s) |
| 6 | 8.25(d, 8.6) | 8.25(d, 8.6) |
| 7 | 8.50(d, 8.6) | 8.50(d, 8.6) |
| 8-OMe | 3.97(s) | 3.97(s) |
| 10-OH | 12.85(s) | 12.85(s) |
| 11 | 7.34(dd, 8.1, 2.3) | 7.34(dd, 8.1, 2.3) |
| 12 | 7.73(m) | 7.73(m) |
| 13 | 7.69(m) | 7.69(m) |
| 15-OH | 15.30(s) | 15.30(s) |
| 17-NH2 | 5.11(br s) | 5.11(br s) |
| 20 | 4.56(q, 7.0) | 4.73(q, 7.0) |
| 22-NH | 8.50(br s) | 8.35(d, 3.9) |
| 23 | 4.34(brs) | 4.12(brs) |
| 24 | 3.84(dd 14.6, 2.8), 4.41(d, 14.6) | 3.42(dd, 14.3, 3.6), 4.59 (d, 14.3) |
| 25-OMe | 3.61(s) | 3.87(s) |
| 26 | 1.32(d, 7.0) | 1.59(d, 7.0) |
| 27 | 1.31(d, 6.3) | 1.31(d, 6.3) |
| 28 | 2.69(m) | 2.69(m) |
| 29 | 1.65(m), 1.78(m) | 1.65(m), 1.78(m) |
| 30 | 0.93(t, 7.2) | 0.93(t, 7.2) |

Bravomicin C

| $^1$H-Position | Rotamer A (50%) | Rotamer B (50%) |
|---|---|---|
| 4 | 6.71(s) | 6.71(s) |
| 6 | 8.25(d, 8.6) | 8.25(d, 8.6) |
| 7 | 8.50(d, 8.6) | 8.50(d, 8.6) |
| 8-OMe | 3.97(s) | 3.97(s) |
| 10-OH | 12.86(s) | 12.86(s) |
| 11 | 7.34(dd, 8.1, 2.3) | 7.34(dd, 8.1, 2.3) |
| 12 | 7.73(m) | 7.73(m) |
| 13 | 7.69(m) | 7.69(m) |
| 15-OH | 15.30(s) | 15.30(s) |
| 17-NH2 | 5.10 (br s) | 5.10(br s) |
| 20 | 4.56(q, 7.0) | 4.73(q, 7.0) |
| 22-NH | 8.50(br s) | 8.35(d, 3.9) |
| 23 | 4.31(br s) | 4.14(br s) |
| 24 | 3.84(dd 14.6, 2.8), 4.41(d, 14.6) | 3.42(dd, 14.3, 3.6), 4.59 (d, 14.3) |
| 25-OEt | 4.08(m) 1.16(t, 7.1) | 4.08(m) 1.16(t, 7.1) |
| 26 | 1.32(d, 7.0) | 1.59(d, 7.0) |
| 27 | 1.31(d, 6.3) | 1.31(d, 6.3) |
| 28 | 2.69(m) | 2.69(m) |
| 29 | 1.65(m), 1.78(m) | 1.65(m), 1.78(m) |
| 30 | 0.93(t, 7.2) | 0.93(t, 7.2) |

Bravomicin D

| Position | Rotamer A (60%) | Rotamer B (40%) |
|---|---|---|
| 4 | 6.71(s) | 6.71(s) |
| 6 | 8.25(d, 8.6) | 8.25(d, 8.6) |
| 7 | 8.50(d, 8.6) | 8.50(d, 8.6) |
| 8-OMe | 4.01(s) | 4.01(s) |
| 10-OH | 12.74(s) | 12.74(s) |
| 11 | 7.34(dd, 8.1, 2.3) | 7.34(d.d, 8.1, 2.3) |
| 12 | 7.73(m) | 7.73(m) |
| 13 | 7.69(m) | 7.69(m) |
| 15-OH | 15.30(s) | 15.30(s) |
| 17-NH2 | 5.11(br s) | 5.11(br s) |
| 20 | 4.38(q, 7.0) | 4 52(q, 7.0) |
| 22-NH | 8.24(br s) | 8.13(d, 3.9) |
| 23 | 4.20(br s) | 4.04(br s) |
| 24 | 3.84(dd 14.1, 3.2), 4.41(d, 14.1) | 3.42(dd, 14.2, 3.2), 4.68 (d, 14.2) |
| 26 | 1.32(d, 7.0) | 1.59(d, 7.0) |
| 27 | 1.31(d, 6.3) | 1.31(d, 6.3) |
| 28 | 2.69(m) | 2.69(m) |
| 29 | 1.52(m), 1.75(m) | 1.52(m), 1.75(m) |
| 30 | 1.25(m), 1.40(m) | 1.25(m), 1.40(m) |
| 31 | 0.85(t, 7.2) | 0.85(t, 7.2) |

Bravomicin E

| Position | Rotamer A (55%) | Rotamer B (45%) |
|---|---|---|
| 4 | 6.71(s) | 6.71(s) |
| 6 | 8.25(d, 8.6) | 8.25(d, 8.6) |
| 7 | 8.50(d, 8.6) | 8.50(d, 8.6) |
| 8-OMe | 4.01(s) | 4.01(s) |
| 10-OH | 12.74(s) | 12.74(s) |
| 11 | 7.34(dd, 8.1, 2.3) | 7.34(dd, 8.1, 2.3) |
| 12 | 7.73(m) | 7.73(m) |
| 13 | 7.69(m) | 7.69(m) |
| 15-OH | 15.30(s) | 15.30(s) |
| 17-NH2 | 5.11(br s) | 5.11 (br s) |
| 20 | 4.38(q, 7.0) | 4.52(q, 7.0) |
| 22-NH | 8.24(br s) | 8.13(d, 3.9) |
| 23 | 4.34(br s) | 4.12(br s) |
| 24 | 3.84(dd 14.6, 2.8), 4.41(d, 14.6) | 3.42(dd, 14.3, 3.6), 4.59 |

TABLE 1-continued

¹H-NMR data of bravomicins

| | | |
|---|---|---|
| | | (d, 14.3) |
| 25-OMe | 3.60(s) | 3.87(s) |
| 26 | 1.32(d, 7.0) | 1.59(d, 7.0) |
| 27 | 1.31(d, 6.3) | 1.31(d, 6.3) |
| 28 | 2.69(m) | 2.69(m) |
| 29 | 1.52(m), 1.75(m) | 1.52(m), 1.75(m) |
| 30 | 1.25(m), 1.40(m) | 1.25(m), 1.40(m) |
| 31 | 0.85(t, 7.2) | 0.85(t, 7.2) |

Bravomicin F

| Position | Rotamer A (50%) | Rotamer B (50%) |
|---|---|---|
| 4 | 6.71(s) | 6.71(s) |
| 6 | 8.25(d, 8.6) | 8.25(d, 8.6) |
| 7 | 8.50(d, 8.6) | 8.50(d, 8.6) |
| 8-OMe | 4.01(s) | 4.01(s) |
| 10-OH | 12.74(s) | 12.74(s) |
| 10-Ac | | |
| 11 | 7.34(dd, 8.1, 2.3) | 7.34(dd, 8.1, 2.3) |
| 12 | 7.73(m) | 7.73(m) |
| 13 | 7.69(m) | 7.69(m) |
| 15-OH | 15.30(s) | 15.30(s) |
| 17-NH2 | 5.11(br s) | 5.11(br s) |
| 20 | 4.38(q, 7.0) | 4.52(q, 7.0) |
| 22-NH | 8.24(br s) | 8.13(d, 3.9) |
| 22-Ac | | |
| 23 | 4.31(br s) | 4.14(br s) |
| 24 | 3.84(dd 14.6, 2.8), 4.41(d, 14.6) (d, 14.3) | 3.42(dd, 14.3, 3.6), 4.59 (d, 14.3) |
| 25-OEt | 4.08(m) | 4.08(m) |
| | 1.16(t, 7.1) | 1.16(t, 7.1) |
| 26 | 1.32(d, 7.0) | 1.59(d, 7.0) |
| 27 | 1.31(d, 6.3) | 1.31(d, 6.3) |
| 28 | 2.69(m) | 2.69(m) |
| 29 | 1.52(m), 1.75(m) | 1.52(m), 1.75(m) |
| 30 | 1.25(m), 1.40(m) | 1.25(m), 1.40(m) |
| 31 | 0.85(t, 7.2) | 0.85(t, 7.2) |

TABLE 2

¹³C-NMR data of bravomicins

Bravomicin A

| ¹³C-Position | Rotamer A (60%) | Rotamer B (40%) |
|---|---|---|
| 1 | 164.3(s) | 164.3(s) |
| 3 | 163.9(s) | 163.9(s) |
| 4 | 97.0(d) | 97.0(d) |
| 4a | 138.5(s) | 138.5(s) |
| 5 | 182.0(s) | 182.0(s) |
| 5a | 133.8(s) | 133.8(s) |
| 6 | 126.8(d) | 126.8(d) |
| 7 | 128.5(d) | 128.5(d) |
| 7a | 137.5(s) | 137.5(s) |
| 8 | 151.9(s) | 151.9(s) |
| 8-OMe | 62.7(q) | 62.7(q) |
| 8a | 119.9(s) | 119.9(s) |
| 9 | 186.3(s) | 186.3(s) |
| 9a | 117.2(s) | 117.2(s) |
| 10 | 161.8(s) | 161.8(s) |
| 11 | 124.7(d) | 124.7(d) |
| 12 | 136.9(d) | 136.9(d) |
| 13 | 118.4(d) | 118.4(d) |
| 13a | 132.6(s) | 132.6(s) |
| 14 | 187.0(s) | 187.0(s) |
| 14a | 109.9(s) | 109.9(s) |
| 15 | 161.0(s) | 161.0(s) |
| 15a | 124.3(s) | 124.3(s) |
| 15b | 141.6(s) | 141.6(s) |
| 16 | 180.7(s) | 180.7(s) |
| 16a | 120.0(s) | 120.0(s) |
| 17 | 157.7(s) | 157.7(s) |
| 18 | 164.7(s) | 164.7(s) |
| 20 | 51.1(d) | 52.7(d) |
| 21 | 168.8(s) | 168.8(s) |
| 23 | 53.2(d) | 52.6(d) |
| 24 | 40.3(t) | 37.1(t) |
| 25 | 172.2(s) | 172.4(s) |
| 26 | 16.0(q) | 17.5(q) |
| 27 | 20.0(q) | 20.0(q) |
| 28 | 38.1(d) | 38.1(d) |
| 29 | 28.3(t) | 28.3(t) |
| 30 | 11.8(q) | 11.8(q) |

Bravomicin diacetate

| ¹³C-Position | Rotamer A (60%) | Rotamer B (40%) |
|---|---|---|
| 1 | 164.0(s) | 164.0(s) |
| 3 | 163.7(s) | 163.7(s) |
| 4 | 97.1(d) | 97.1(d) |
| 4a | 138.5(s) | 138.5(s) |
| 5 | 182.1(s) | 182.1(s) |
| 5a | 133.5(s) | 133.5(s) |
| 6 | 126.4(d) | 126.4(d) |
| 7 | 128.3(d) | 128.3(d) |
| 7a | 137.5(s) | 137.5(s) |
| 8 | 150.8(s) | 150.8(s) |
| 8-OMe | 62.9(q) | 62.9(q) |
| 8a | 120.5(s) | 120.5(s) |
| 9 | 180.1(s) | 180.1(s) |
| 9a | 126.6(s) | 126.6(s) |
| 10 | 149.4(s) | 149.4(s) |
| 10-Ac | 169.3(s) | 169.3(s) |
| | 21.1(q) | 21.1(q) |
| 11 | 130.8(d) | 130.8(d) |
| 12 | 135.0(d) | 135.0(d) |
| 13 | 124.8(d) | 124.8(d) |
| 13a | 134.2(s) | 134.2(s) |
| 14 | 186.9(s) | 186.9(s) |
| 14a | 110.1(s) | 110.1(s) |
| 15 | 160.2(s) | 160.2(s) |
| 15a | 123.6(s) | 123.6(s) |
| 15b | 141.7(s) | 141.7(s) |
| 16 | 180.9(s) | 180.9(s) |
| 16a | 119.9(s) | 119.9(s) |
| 17 | 157.8(s) | 157.8(s) |
| 18 | 164.2(s) | 164.2(s) |
| 20 | 52.9(d) | 54.2(d) |
| 21 | 170.6(s) | 170.7(s) |
| 22-Ac | 172.9(s) | 172.6(s) |
| | 27.3(q) | 27.3(q) |
| 23 | 55.9(d) | 55.7(d) |
| 24 | 41.5(t) | 37.3(t) |
| 25 | 170.7(s) | 170.7(s) |
| 26 | 16.6(q) | 18.0(q) |
| 27 | 20.0(q) | 20.0(q) |
| 28 | 38.2(d) | 38.2(d) |
| 29 | 28.6(t) | 28.6(t) |
| 30 | 11.7(q) | 11.7(q) |

Bravomicin B

| ¹³C-Position | Rotamer A (55%) | Rotamer B (45%) |
|---|---|---|
| 1 | 164.1(s) | 164.1(s) |
| 3 | 163.9(s) | 163.9(s) |
| 4 | 97.1(d) | 97.1(d) |
| 4a | 138.7(s) | 138.7(s) |
| 5 | 182.1(s) | 182.1(s) |
| 5a | 134.0(s) | 134.0(s) |
| 6 | 126.9(d) | 126.9(d) |
| 7 | 128.5(d) | 128.5(d) |
| 7a | 137.6(s) | 137.6(s) |
| 8 | 151.9(s) | 151.9(s) |
| 8-OMe | 62.8(q) | 62.8(q) |
| 8a | 119.7(s) | 119.7(s) |
| 9 | 186.7(s) | 186.7(s) |
| 9a | 117.5(s) | 117.5(s) |

TABLE 2-continued

¹³C-NMR data of bravomicins

| Position | Rotamer A | Rotamer B |
|---|---|---|
| 10 | 161.8(s) | 161.8(s) |
| 11 | 124.7(d) | 124.7(d) |
| 12 | 136.9(d) | 136.9(d) |
| 13 | 118.6(d) | 118.6(d) |
| 13a | 132.9(s) | 132.9(s) |
| 14 | 187.4(s) | 187.4(s) |
| 14a | 110.3(s) | 110.3(s) |
| 15 | 161.1(s) | 161.1(s) |
| 15a | 124.6(s) | 124.6(s) |
|  | 141.9(s) | 141.9(s) |
| 16 | 180.8(s) | 180.8(s) |
| 16a | 120.3(s) | 120.3(s) |
| 17 | 157.9(s) | 157.9(s) |
| 18 | 164.9(s) | 164.9(s) |
| 20 | 51.1(d) | 52.8(d) |
| 21 | 168.9(s) | 168.8(s) |
| 23 | 53.2(d) | 52.7(d) |
| 24 | 40.5(t) | 37.5(t) |
| 25 | 171.4(s) | 171.4(s) |
| 25-OMe | 52.0(q) | 53.1(q) |
| 26 | 15.9(q) | 17.3(q) |
| 27 | 20.0(q) | 20.0(q) |
| 28 | 38.1(d) | 38.1(d) |
| 29 | 28.3(t) | 28.3(t) |
| 30 | 11.5(q) | 11.5(q) |

Bravomicin C

| ¹³C-Position | Rotamer A | Rotamer B |
|---|---|---|
| 1 | 164.3(s) | 164.3(s) |
| 3 | 163.9(s) | 163.9(s) |
| 4 | 97.0(d) | 97.0(d) |
| 4a | 138.5(s) | 138.5(s) |
| 5 | 182.0(s) | 182.0(s) |
| 5a | 133.8(s) | 133.8(s) |
| 6 | 126.8(d) | 126.8(d) |
| 7 | 128.5(d) | 128.5(d) |
| 7a | 137.5(s) | 137.5(s) |
| 8 | 151.9(s) | 151.9(s) |
| 8-OMe | 62.7(q) | 62.7(q) |
| 8a | 119.9(s) | 119.9(s) |
| 9 | 186.3(s) | 186.3(s) |
| 9a | 117.2(s) | 117.2(s) |
| 10 | 161.8(s) | 161.8(s) |
| 11 | 124.7(d) | 124.7(d) |
| 12 | 136.9(d) | 136.9(d) |
| 13 | 118.4(d) | 118.4(d) |
| 13a | 132.6(s) | 132.6(s) |
| 14 | 187.0(s) | 187.0(s) |
| 14a | 109.9(s) | 109.9(s) |
| 15 | 161.0(s) | 161.0(s) |
| 15a | 124.3(s) | 124.3(s) |
| 15b | 141.6(s) | 141.6(s) |
| 16 | 180.7(s) | 180.7(s) |
| 16a | 120.0(s) | 120.0(s) |
| 17 | 157.7(s) | 157.7(s) |
| 18 | 164.7(s) | 164.7(s) |
| 20 | 51.1(d) | 52.8(d) |
| 21 | 168.9(s) | 168.8(s) |
| 23 | 53.2(d) | 52.7(d) |
| 24 | 40.5(t) | 37.5(t) |
| 25 | 171.4(s) | 171.4(s) |
| 25-OEt | 61.5(t) | 61.5(t) |
|  | 13.9(q) | 13.9(q) |
| 26 | 15.9(q) | 17.3(q) |
| 27 | 20.0(q) | 20.0(q) |
| 28 | 38.1(d) | 38.1(d) |
| 29 | 28.3(t) | 28.3(t) |
| 30 | 11.8(q) | 11.8(q) |

Bravomicin D

| Position | Rotamer A (60%) | Rotamer B (40%) |
|---|---|---|
| 1 | 164.3(s) | 164.3(s) |
| 3 | 163.9(s) | 163.9(s) |
| 4 | 97.0(d) | 97.0(d) |
| 4a | 138.5(s) | 138.5(s) |
| 5 | 182.0(s) | 182.0(s) |
| 5a | 133.8(s) | 133.8(s) |
| 6 | 126.8(d) | 126.8(d) |
| 7 | 128.5(d) | 128.5(d) |
| 7a | 137.5(s) | 137.5(s) |
| 8 | 151.9(s) | 151.9(s) |
| 8-OMe | 62.7(q) | 62.7(q) |
| 8a | 119.9(s) | 119.9(s) |
| 9 | 186.3(s) | 186.3(s) |
| 9a | 117.2(s) | 117.2(s) |
| 10 | 161.8(s) | 161.8(s) |
| 11 | 124.7(d) | 124.7(d) |
| 12 | 136.9(d) | 136.9(d) |
| 13 | 118.4(d) | 118.4(d) |
| 13a | 132.6(s) | 132.6(s) |
| 14 | 187.0(s) | 187.0(s) |
| 14a | 109.9(s) | 109.9(s) |
| 15 | 161.0(s) | 161.0(s) |
| 15a | 124.3(s) | 124.3(s) |
| 15b | 141.6(s) | 141.6(s) |
| 16 | 180.7(s) | 180.7(s) |
| 16a | 120.0(s) | 120.0(s) |
| 17 | 157.7(s) | 157.7(s) |
| 18 | 164.7(s) | 164.7(s) |
| 20 | 51.1(d) | 52.7(d) |
| 21 | 168.8(s) | 168.8(s) |
| 23 | 53.2(d) | 52.6(d) |
| 24 | 40.3(t) | 37.1(t) |
| 25 | 172.2(s) | 172.4(s) |
| 26 | 16.0(q) | 17.5(q) |
| 27 | 20.0(q) | 20.0(q) |
| 28 | 36.9(d) | 36.9(d) |
| 29 | 38.8(t) | 38.8(t) |
| 30 | 20.6(t) | 20.6(t) |
| 31 | 14.2(q) | 14.2(q) |

Bravomicin E

| Position | Rotamer A (55%) | Rotamer B (45%) |
|---|---|---|
| 1 | 164.1(s) | 164.1(s) |
| 3 | 163.9(s) | 163.9(s) |
| 4 | 97.1(d) | 97.1(d) |
| 4a | 138.7(s) | 138.7(s) |
| 5 | 182.1(s) | 182.1(s) |
| 5a | 134.0(s) | 134.0(s) |
| 6 | 126.9(d) | 126.9(d) |
| 7 | 128.5(d) | 128.5(d) |
| 7a | 137.6(s) | 137.6(s) |
| 8 | 151.9(s) | 151.9(s) |
| 8-OMe | 62.8(q) | 62.8(q) |
| 8a | 119.7(s) | 119.7(s) |
| 9 | 186.7(s) | 186.7(s) |
| 9a | 117.5(s) | 117.5(s) |
| 10 | 161.8(s) | 161.8(s) |
| 11 | 124.7(d) | 124.7(d) |
| 12 | 136.9(d) | 136.9(d) |
| 13 | 118.6(d) | 118.6(d) |
| 13a | 132.9(s) | 132.9(s) |
| 14 | 187.4(s) | 187.4(s) |
| 14a | 110.3(s) | 110.3(s) |
| 15 | 161.1(s) | 161.1(s) |
| 15a | 124.6(s) | 124.6(s) |
| 15b | 141.9(s) | 141.9(s) |
| 16 | 180.8(s) | 180.8(s) |
| 16a | 120.3(s) | 120.3(s) |
| 17 | 157.9(s) | 157.9(s) |
| 18 | 164.9(s) | 164.9(s) |
| 20 | 51.1(d) | 52.8(d) |
| 21 | 168.9(s) | 168.8(s) |
| 23 | 53.2(d) | 52.7(d) |
| 24 | 40.5(t) | 37.5(t) |
| 25 | 171.4(s) | 171.4(s) |
| 25-OMe | 52.0(q) | 53.1(q) |
| 26 | 15.9(q) | 17.3(q) |

TABLE 2-continued $^{13}$C-NMR data of bravomicins

| | | |
|---|---|---|
| 27 | 20.0(q) | 20.0(q) |
| 28 | 36.9(d) | 36.9(d) |
| 29 | 38.8(t) | 38.8(t) |
| 30 | 20.6(t) | 20.6(t) |
| 31 | 14.2(q) | 14.2(q) |

| | Bravomicin F | |
|---|---|---|
| Position | Rotamer A (50%) | Rotamer B (50%) |
| 1 | 164.3(s) | 164.3(s) |
| 3 | 163.9(s) | 163.9(s) |
| 4 | 97.0(d) | 97.0(d) |
| 4a | 138.5(s) | 138.5(s) |
| 5 | 182.0(s) | 182.0(s) |
| 5a | 133.8(s) | 133.8(s) |
| 6 | 126.8(d) | 126.8(d) |
| 7 | 128.5(d) | 128.5(d) |
| 7a | 137.5(s) | 137.5(s) |
| 8 | 151.9(s) | 151.9(s) |
| 8-OMe | 62.7(q) | 62.7(q) |
| 8a | 119.9(s) | 119.9(s) |
| 9 | 186.3(s) | 186.3(s) |
| 9a | 117.2(s) | 117.2(s) |
| 10 | 161.8(s) | 161.8(s) |
| 11 | 124.7(d) | 124.7(d) |
| 12 | 136.9(d) | 136.9(d) |
| 13 | 118.4(d) | 118.4(d) |
| 13a | 132.6(s) | 132.6(s) |
| 14 | 187.0(s) | 187.0(s) |
| 14a | 109.9(s) | 109.9(s) |
| 15 | 161.0(s) | 161.0(s) |
| 15a | 124.3(s) | 124.3(s) |
| 15b | 141.6(s) | 141.6(s) |
| 16 | 180.7(s) | 180.7(s) |
| 16a | 120.0(s) | 120.0(s) |
| 17 | 157.7(s) | 157.7(s) |
| 18 | 164.7(s) | 164.7(s) |
| 20 | 51.1(d) | 52.8(d) |
| 21 | 168.9(s) | 168.8(s) |
| 23 | 53.2(d) | 52.7(d) |
| 24 | 40.5(t) | 37.5(t) |
| 25 | 171.4(s) | 171.4(s) |
| 25-OEt | 61.5(t) | 61.5(t) |
| | 13.9(q) | 13.9(q) |
| 26 | 15.9(q) | 17.3(q) |
| 27 | 20.0(q) | 20.0(q) |
| 28 | 36.9(d) | 36.9(d) |
| 29 | 38.8(t) | 38.8(t) |

TABLE 2-continued $^{13}$C-NMR data of bravomicins

| | | |
|---|---|---|
| 30 | 20.6(t) | 20.6(t) |
| 31 | 14.2(q) | 14.2(q) |

It should be noted that the bravomicins are capable of forming acidic and/or basic salts with inorganic or organic acids and bases. For example, bravomicin A or D may be converted into their respective alkali metal or amine salts by treatment with alkali metal hydroxide or amine, respectively. Preferably, bravomicins A and D are converted to their respective sodium or triethylamine salts by treatment with sodium hydroxide or triethylamine, preferably by reacting one molar equivalent of base per mole of bravomicin component in water followed by lyophilization to yield water-soluble salts of bravomicins A and D in which the carboxylic moiety at carbon-25 is converted to the moiety COONa or COO(Et$_3$N). It is intended that the present invention encompasses all pharmaceutically acceptable salts of the bravomicin components.

The acylated derivatives at amino or phenolic groups of the bravomicins described herein may be prepared by contacting bravomicin A, B, C, D, E or F with conventional acylation reagents such as acid halides, preferably acid chlorides, or acid anhydrides in the presence of an organic base such as pyridine or 4-dimethylaminopyridine to effect acylation and form the ester and amide moieties, preferably at the phenolic group of position 10 and the amido group at position 22. Preferably, the bravomicins are converted to their respective acetyl, benzoyl or cyclohexanecarbonyl esters by treatment with acetyl anhydride, benzoyl chloride or cyclohexanecarbonyl chloride. It is intended that the acylated derivatives of the bravomicins of the present invention are encompassed by the present invention.

Biological Activity Data

To demonstrate their antibacterial properties, the minimum inhibitory concentration (MIC) for bravomicin A, bravomicin A diacetate, bravomicin B and bravomicin C was obtained against a variety of bacteria using a conventional broth dilution assay (serial broth dilution method using nutrient broth (Difco). The results obtained are shown in Table 3 below and demonstrate that bravomicin A, B and C have utility in treating bacterial infections.

TABLE 3

| | | MIC(ug/ml) | | | |
|---|---|---|---|---|---|
| Organism | Strain # | Bravomicin A | Bravomicin B | Bravomicin C | Bravomicin A diacetate |
| Streptococcus pneumoniae | A9585 | 0.125 | 0.015 | 0.125 | 0.03 |
| S. pneumoniae | A27881 | 0.125 | 0.007 | 0.06 | 0.03 |
| S. pneumoniae /start penicillin resistant | A28272 | 0.125 | 0.007 | 0.06 | 0.03 |
| Streptococcus pyogenes | A9604 | 0.125 | n.t. | n.t. | n.t. |
| Enterococcus faecalis | A20688 | 0.03 | 0.03 | 0.50 | 0.125 |
| Enterococcus faecalis + 50% calf serum | A20688 | 0.03 | n.t. | n.t. | n.t. |
| Enterococcus faecium | A24885 | 0.5 | 0.06 | 0.50 | 0.5 |

TABLE 3-continued

| Organism | Strain # | MIC(ug/ml) Bravomicin A | Bravomicin B | Bravomicin C | Bravomicin A diacetate |
|---|---|---|---|---|---|
| *Enterococcus faecium*/ ampicillin resistant | A28156 | 0.5 | n.t. | n.t. | n.t. |
| *Staphylococcus aureus* | A9537 | 0.015 | n.t. | n.t. | n.t. |
| *S. aureus* | A9497 | 0.015 | n.t. | n.t. | n.t. |
| *S. aureus* | A9606 | 0.03 | n.t. | n.t. | n.t. |
| *S. aureus* + 50% calf serum | A9606 | 0.06 | n.t. | n.t. | n.t. |
| *S. aureus* | A15960 | 0.03 | n.t. | n.t. | n.t. |
| *S. aureus* + 50% calf serum | A15960 | 0.06 | n.t. | n.t. | n.t. |
| *S. aureus* | A20241 | 0.03 | n.t. | n.t. | n.t. |
| *S. aureus*/ hetero methicillin resistant | A27218 | 0.03 | n.t. | n.t. | n.t. |
| *S. aureus* + 50% calf serum | A27218 | 0.06 | n.t. | n.t. | n.t. |
| *S. aureus*/ hetero methicillin resistant | A27217 | 0.03 | n.t. | n.t. | n.t. |
| *S. aureus*/ hetero methicillin resistant | A25795 | 0.06 | n.t. | n.t. | n.t. |
| *S. aureus*/ homo methicillin resistant | A27223 | 0.06 | n.t. | n.t. | n.t. |
| *S. aureus* + 50% calf serum | A27223 | 0.06 | n.t. | n.t. | n.t. |
| *S. aureus* /homo methicillin resistant | A27621 | 0.06 | n.t. | n.t. | n.t. |
| *S. aureus* /homo methicillin resistant | A27295 | 0.06 | n.t. | n.t. | n.t. |
| *S. aureus* /homo methicillin resistant | A27226 | 0.06. | n.t. | n.t. | n.t. |
| *S. aureus*/ methicillin resistant | A27225 | 0.06 | n.t. | n.t. | n.t. |
| *S. epidermidis* | A24548 | 0.015 | n.t. | n.t. | n.t. |
| *S. epidermidis*/methicillin resistant | A25783 | 0.03 | n.t. | n.t. | n.t. |
| *S. epidermidis*/imipenem resistant | A27368 | 0.03 | n.t. | n.t. | n.t. |
| *S. haemolyticus* | A21638 | 0.03 | n.t. | n.t. | n.t. |
| *S. haemolyticus*/hetero methicillin resistant | A27235 | 0.03 | n.t. | n.t. | n.t. |
| *S. haemolyticus*/homo methicillin resistant | A27229 | 0.03 | n.t. | n.t. | n.t. |

TABLE 3-continued

| Organism | Strain # | MIC(ug/ml) Bravomicin A | Bravomicin B | Bravomicin C | Bravomicin A diacetate |
|---|---|---|---|---|---|
| S. haemolyticus/homo methicillin resistant | A27231 | 0.03 | n.t. | n.t. | n.t. |
| S. haemolyticus/homo methicillin resistant | A27228 | 0.03 | n.t. | n.t. | n.t. |
| Esherichia coli | A15119 | >128 | >128 | >128 | >128 |
| Moraxella catarrhalis | A22344 | 4 | n.t. | n.t. | n.t. |
| Haemophilus influenzae | A20191 | 4 | n.t. | n.t. | n.t. |
| Klebsiella pneumoniae | A9664 | >128 | n.t. | n.t. | n.t. |
| Enterobacter cloacae | A9656 | 64 | n.t. | n.t. | n.t. |
| Proteus mirabilis | A9900 | 64 | n.t. | n.t. | n.t. |
| Pseudomonas aeruginosa | A9843 | 64 | n.t. | n.t. | n.t. |
| Salmonella typhimurium | A27207 | >128 | >128 | >128 | >128 |
| Salmonella typhimurium Re LPS | A27208 | 0.5 | 2 | 8 | 8 | n.t. not tested

Bravomicins were also found to be bactericidal. Table 4 below shows the MIC and minimum bactericidal concentration (MBC) of bravomicin A against a selected group of bacteria.

TABLE 4

| Organism | Strain # | MIC(ug/ml) | MBC(ug/ml) |
|---|---|---|---|
| Streptococcus pneumoniae | A9585 | 0.125 | 0.125 |
| S. pneumoniae | A27881 | 0.06 | 0.06 |
| S. pneumoniae/penicillin resistant | A28272 | 0.125 | 0.125 |
| Enterococcus faecalis | A20688 | 0.015 | 0.06 |
| Enterococcus faecium | A24885 | 0.125 | 0.125 |
| S. aureus | A9606 | 0.03 | 0.06 |
| S. aureus/homo methicillin resistant | A27223 | 0.06 | 0.06 |
| Haemophilus influenzae | A20191 | 16 | 16 |
| Salmonella typhimurium | A27207 | >128 | >128 |
| Salmonella typhimurium Re LPS | A27208 | 0.5 | 2 |

The antibiotics of the present invention display antibacterial activity against a variety of bacteria. They are especially valuable against certain resistant strains of gram-positive bacteria shown above such as methicillin-resistant *Staphylococcus aureus* (MRSA) and multiply resistant *Enterococcus faecium*. Significantly, the bravomicins are also bactericidal against certain clinically important bacterial strains.

The present invention includes within its scope pharmaceutical compositions containing an effective antibacterial amount of bravomicin A, B, C, D, E or F, or a pharmaceutically acceptable ester and/or salt thereof, in combination with an inert pharmaceutically acceptable carrier. The compositions may also contain other active antibacterial agents. Such compositions may be made up in any pharmaceutical form appropriate for the route of administration in question. Examples of such compositions include solid compositions for oral administration such as tablets, capsules, pills, powders and granules, liquid compositions for oral administration such as solutions, suspensions, syrups and elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antibacterial agent, the compound of the present invention is administered so that the concentration of active ingredient is greater than the minimum inhibitory concentration for the particular organism being treated. It will of course be appreciated that the actual dose of bravomicin used will be determined by the physician or veterinarian after consideration of such factors as age, body weight, sex, diet, route of administration, rate of excretion, condition of the patient, drug combinations, and the particular situs and disease being treated.

The following examples serve to illustrate the invention without limiting it. Sephadex LH-20 is the trade name of Pharmacia Fine Chemicals, Inc. for an alkylated cross-linked dextran used in absorption and gel filtration chromatography. YMC*Gel ODS-120A is a product of YMC, Inc., Wilmington, N.C.

Description of a MREF Assay Procedure

The biological activity of the bravomicins was discovered when a crude extract prepared from the producing *Micromonospora polytrota* ATCC-202091 culture was tested in a high throughput screening assay. The screen is based on growth inhibition of *Enterococcus faecium* strain A28152 inoculated into agar growth media. This *E. faecium* strain is resistant to many antibiotics, including penicillin G, vancomycin, ciprofloxacin, teicoplanin, tetracycline, streptomycin, gentamicin, erythromycin, clindamycin and rifampin. It is sensitive to chloramphenicol and, to a lesser extent, imipenem. Hence the name MREF, which stands for Multi-drug Resistant *E. faecium*.

*E. faecium* strain A28152 is inoculated into Luria Broth nutrient medium and cultured to log phase growth by incubation at 37° C. with agitation. Periodically, 0.2 mL aliquots of culture are withdrawn and pipetted into a well in a 96 well clear plastic flat-bottom plate. The optical density at 595 nm is then measured. When the optical density is in the range of 0.2 to 0.4, the bacteria are harvested by centrifugation at 1000×g for 10 minutes. The cell pellet is resuspended in Mueller-Hinton II growth media. This suspension of cells is then inoculated into molten Mueller-Hinton II growth media containing 1% Difco agar at a temperature of 480° C., to give an inoculated cell density of $1\times10^7$ cells/mL. 25 mL of the cell suspension is poured into a sterile rectangular plate. A special sterile plastic lid that mates with the plate is placed on top of the plate while the media is still molten. This lid contains plastic pegs arranged in the standard 8×12 format. The media is allowed to gel at room temperature for 15 minutes, then the pin lid is removed. Small concave impressions remain in the gelled media where the pins contacted the surface of the molten media. These serve as sample loading zones.

Samples to be tested in the screen are dissolved to a concentration of 300 μM in 100% DMSO. A 6 μL volume of each sample is applied to individual sample loading zones on the plate. After sample loading, the plate is incubated at 37° C. for 24 hours. Growth inhibition is detected as a clear circular zone surrounding the sample zone. Outside of this zone, where the bacterial growth is unimpeded, the agar medium is turbid due to bacterial growth. DMSO alone does not cause any detectable growth inhibition under these conditions. Samples of chloramphenicol and DMSO are included on each plate as positive and negative controls, respectively.

Analytical TLC:

Kieselgel 60 F254, a silica gel precoated thin layer chromatography on aluminum sheet, (20×20 cm) was purchased from Bodman Co., Aston, Pa. The plates were developed in a tank equilibrated with chloroform/methanol (9:1 v/v) with one drop of acetic acid. The components of the resulting chromatogram were detected under a UV light.

Analytical HPLC:

The purification of the bravomicins were monitored by HPLC analysis on an Inertsil 5μ ODS-2 column, 4.6 mm i.d.×25 cm l. (MetaChem Technologies Inc., Torrance, Calif.). Analyses were done on a Hewlett Packard 1090 Liquid Chromatograph, equipped with a model 8452 photodiode array spectrophotometer set at 254 and 280 nm, and ChemStation (Revision A.04.02) operating software. A gradient solvent system consisting of acetonitrile and 0.1% trifluoroacetic acid was used at a flow rate of 1.2 ml/min with a run time of 32 minutes. The gradient table is shown below:

| Time (min) | acetonitrile (%) | 0.1% CF$_3$COOH in water (%) |
|---|---|---|
| 0.00 | 55 | 45 |
| 6.00 | 55 | 45 |
| 12.00 | 60 | 40 |
| 19.00 | 85 | 15 |
| 32.00 | 85 | 15 |

Preparative HPLC:

The following components were used to construct a preparative HPLC system: Dynamax SD-200 pumps, Dynamax dual wavelength spectrophotometer UV-D11 and Dynamax method manager software (Rainin Instruments, Woburn, Mass.). Inertsil ODS-2 column, 5 μ, 20 mm i.d.×25 cm l. plus 10 mm i.d.×5 cm l. guard column (MetaChem Technologies Inc., Torrance, Calif.). Two gradient solvent systems consisting of acetonitrile and 0.1% trifluoroacetic acid were used at a flow rate of 10 ml/min with run time of 40 minutes, respectively. The bravomicins were detected by monitoring the eluate stream at 254 nm.

EXAMPLE 1

Preparation of Bravomicins A, B and C

A. Cultivation of Producing Microorganism

A culture of *Micromonospora polytrota* ATCC-202091 was grown in a 500 ml flask containing 100 ml of vegetative medium consisting of the following per liter of tap water: starch, 20 g; dextrose, 5 g; N-Z case, 3 g; yeast extract, 2 g; fish meat extract, 5 g; calcium carbonate, 3 g. The culture was allowed to incubate for 4 days at 28° C. on a rotary shaker operating at 250 rpm. The vegetative culture was mixed with equal volume of cryoprotective solution consisting of 100 g sucrose and 200 g glycerol per liter of deionized water. Four ml portions of this mixture were transferred to sterile cryogenic tube (5 ml capacity) and were frozen in a dry ice-acetone bath. The frozen vegetative cultures so obtained were then stored at −80° C.

Seed culture for the production of bravomicins was prepared by transferring 4 ml of the cryopreservative culture to a 500 ml flask containing 100 ml of sterile medium having the same composition as the vegetative medium described above. The seed culture was incubated at 28° C. for 3 days on a rotary shaker operating at 250 rpm. Five ml of this seed culture was inoculated into 500 ml flask containing 100 ml of production medium consisting of the following per liter of tap water: soluble starch, 10 g; Pharmamedia, 5 g; calcium carbonate, 1 g. The production culture was incubated at 28° C. on a rotary shaker operating at 250 rpm to provide optimal production of bravomicins at 7 days of fermentation.

B. Preparation of Crude Extract A:

Fermentation broth of *Micromonospora polytrota* ATCC-202091 (10 L.) was centrifuged in a 1-L plastic bucket on a Beckman J-6B centrifugate at 2100×g for 20 minutes. The supernatant was removed by decanting from the bucket, and to each bucket containing precipitates of mycelia 500 ml of chloroform-methanol solvent mixture (1:1) was added and the suspension was stirred for 30 min. The suspension was combined, mixed with approximately 500 g of dicalite and filtered by vacuum filtration using a large Coors Buchner funnel (27 cm i.d., 28.5 cm o.d., 9 cm deep). The brown organic layer was evaporated in vacuo to dryness in a rotary evaporator to yield approximately 15 g of Residue A.

C. Liquid-Liquid Partition of Residue A:

Residue A (15 g) was dissolved in 800 ml chloroform/methanol/water mixture (2:2:1, biphasic). The solution was partitioned in a 1000 ml separatory funnel. Bravomicins were concentrated primarily in the lower layer. The brown lower layer was collected, and evaporated in vacuo to dryness in a rotary evaporator. The residue was dissolved in 50 ml of methanol and 6 ml of water, and extracted 3 times with an equal volume of hexane. The hexane layer was removed. Bravomicins were concentrated primarily in the aqueous methanol layer. The aqueous methanol layer was evaporated to dryness in vacuo in a rotary evaporator to give 2.3 g of Residue B.

D. Sephadex LH-20 Chromatography of Residue B:

Residue B (2.3 g) was dissolved in 5 ml chloroform and mixed with 5 g of Sephadex LH-20, the mixture was dried by air and applied onto a 3×100 cm Spectrum column packed with 300 g Sephadex LH-20 in 70% aqueous methanol. Fractions measuring 8–10 ml each were collected at a flow rate of 2–3 ml/min. Fractions were consolidated on the basis of silica TLC profile (chloroform/methanol 9:1, trace acetic acid), TLC bioautography and HPLC bioautography. In this manner, active fractions containing bravomicins were detected, combined and evaporated to dryness to yield Residue C 245 mg and Residue D 80 mg.

E. Preparative HPLC of Residue C and Residue D:

Further purification of bravomicin-enriched fraction (Residues C and D) was accomplished by using the specified Rainin Dynamax preparative HPLC system. A typical injection sample size was 8 mg/0.4 ml DMSO. Elution flow rate was 10 ml/min. Detection (UV) was at 254 nm. Sixty mg of Residue C were purified with the following solvent gradient:

| Time (min) | acetonitrile (%) | 0.1% $CF_3COOH$ in water (%) |
|---|---|---|
| 0.00 | 55 | 45 |
| 6.00 | 55 | 45 |
| 15.00 | 85 | 15 |
| 32.00 | 85 | 15 |
| 40.00 | 55 | 45 |

The major peak (16.6 min) was collected and the solvent removed in vacuo to yield 10 mg pure bravomicin A.

Seventy two mg of Residue D were purified by the specified Rainin Dynamax preparative HPLC system with the following solvent gradient:

| Time (min) | acetonitrile (%) | 0.1% $CF_3COOH$ in water (%) |
|---|---|---|
| 0.00 | 55 | 45 |
| 10.00 | 65 | 35 |
| 25.00 | 75 | 25 |
| 35.00 | 75 | 25 |
| 38.00 | 85 | 15 |
| 40.00 | 85 | 15 |

Peaks were collected, and the eluate was kept at a −20° C. refrigerator for 5 hours to allow biphasic formation into upper layer of acetonitrile and lower frozen layer of water. The reddish orange upper layer was taken out and the solvent removed in vacuo to give purified bravomicins. In this manner, the following compounds were obtained, bravomicin A [6.6 mg, retention time (Rt) at 16.7 min], bravomicin D [3.0 mg, Rt at 20.3 min], bravomicin B [7.7 mg, Rt at 21.6 min], bravomicin C [4.6 mg, Rt at 24.6 min], bravomicin E [2.2 mg, Rt at 25.7 min], and bravomicin F [1.8 mg, Rt at 29.0 min].

EXAMPLE 2

Acetylation of Bravomicin A

Bravomicin A enriched fraction (Residue C, 140 mg) as obtained in Example 1 was dissolved in 2.5 ml of pyridine, and to the solution 1.2 ml of acetic anhydride was added at 0° C. The reaction mixture was monitored by TLC (chloroform/methanol 9:1, trace acetic acid). After 5 hours at room temperature, a mixture of methanol (2 ml) and water (4 ml) was added, and the solution was extracted with ethyl acetate (10 ml each) three times, and the ethyl acetate layer was evaporated to dryness in vacuo in a rotary evaporator to give 180 mg of Residue E. Residue E (165 mg) was purified by the specified Rainin Dynamax preparative HPLC system with the following solvent gradient.

| Time (min) | acetonitrile (%) | 0.1% $CF_3COOH$ in water (%) |
|---|---|---|
| 0.00 | 55 | 45 |
| 5.00 | 60 | 40 |
| 15.00 | 60 | 40 |
| 23.00 | 65 | 35 |
| 34.00 | 70 | 30 |
| 40.00 | 75 | 25 |

A major peak at 25.0 min was collected, and the eluate was kept at a −200° C. refrigerator for 5 hours to allow biphasic formation. The reddish orange acetonitrile upper layer was taken out and the solvent removed in vacuo to give 31 mg of bravomicin A diacetate.

Bravomicin A diacetate, a reddish orange amorphous powder, is soluble in DMSO, chloroform, methanol, acetone, but insoluble in hexane. The compound has been found to be an inseparable rotameric mixture (60%:40%) and have the following characteristics: molecular formula $C_{42}H_{35}N_3O_{14}$; UV (MeOH) λ max (log ε) 253 (4.60), 286 (sh., 4.48), 324 (4.24), 460 (4.20) nm; IR (KBr) ν max 3448, 2968, 1768, 1670, 1640, 1561, 1448, 1420, 1372, 1283, 1256, 1229, 1197, 1043, 986, 951, 753 $cm^{+1}$; Positive electrospray MS (relative intensity %) m/z:828 (80, [M+Na]$^+$), 806 (72, [M+H]$^+$); Negative electrospray MS (relative intensity %) m/z: 804 (20, [M−H]$^−$); $^1$H-NMR spectrum (500 MHz) in DMSO-$d_6$ in Table 1. $^{13}$C-NMR spectrum (125 MHz) in DMSO-$d_6$ in Table 2.

We claim:

1. A compound selected from a compound of the formula

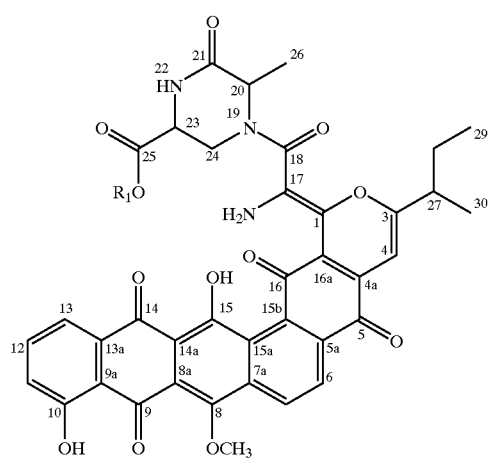

in which (a) $R_1$ is hydrogen (bravomicin A);
(b) $R_1$ is —$CH_3$ (bravomicin B);
(c) $R_1$ is —$CH_2CH_3$ (bravomicin C); or

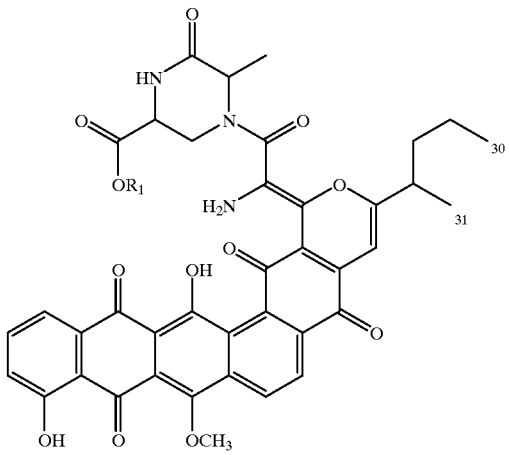

in which (d) $R_1$ is hydrogen (bravomicin D);
(e) $R_1$ is —$CH_3$ (bravomicin E); and
(f) $R_1$ is —$CH_2CH_3$ (bravomicin F); or a pharmaceutically acceptable salt or ester thereof.

2. The compound bravomicin A represented by the structure

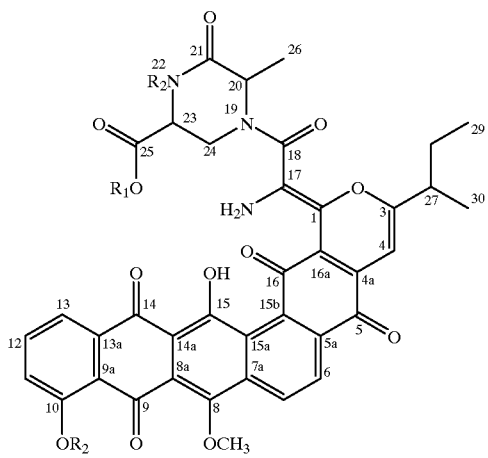

in which $R_1$ and $R_2$ are hydrogen, or a pharmaceutically acceptable salt or ester thereof.

3. The diacetate ester of the compound of claim 2 in which $R_2$ is —$COCH_3$.

4. The compound bravomicin B represented by the structure

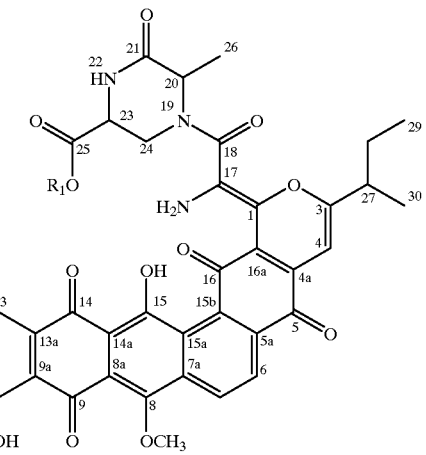

in which $R_1$ is —$CH_3$, or a pharmaceutically acceptable salt or ester thereof.

5. The compound bravomicin C represented by the structure

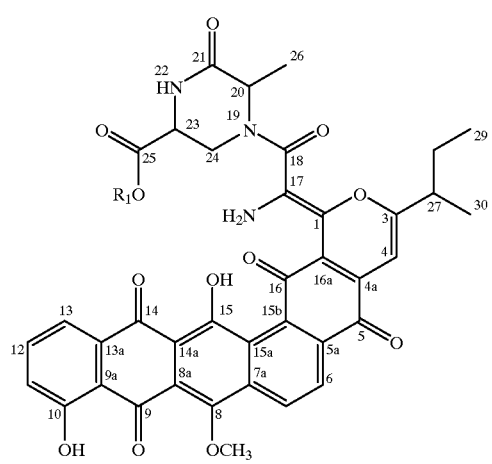

in which $R_1$ is —$CH_2CH_3$, or a pharmaceutically acceptable salt or ester thereof.

6. The compound bravomicin D having the formula

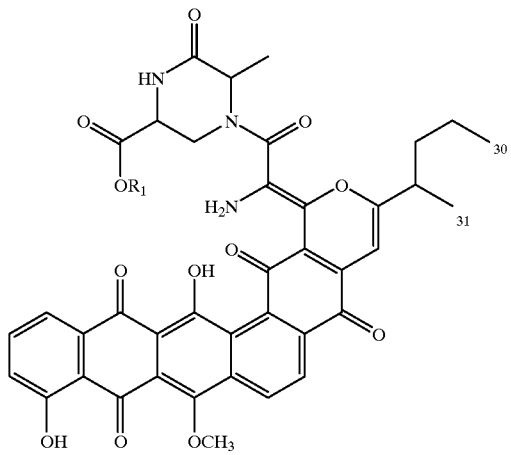

in which $R_1$ is hydrogen; or a pharmaceutically acceptable salt or ester thereof.

7. The compound bravomicin E having the formula

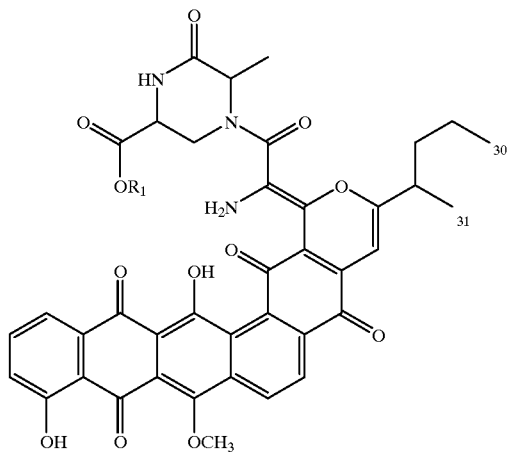

in which $R_1$ is —$CH_3$, or a pharmaceutically acceptable salt or ester thereof.

8. The compound bravomicin F having the formula

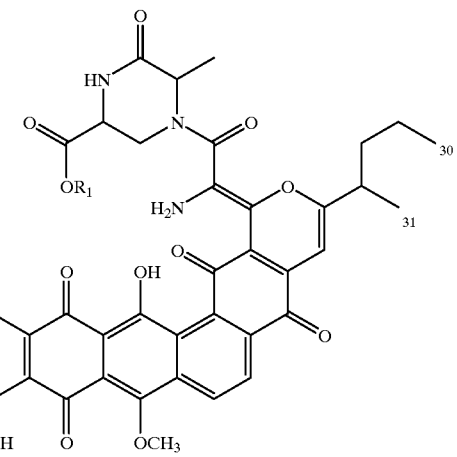

in which $R_1$ is —$CH_2CH_3$, or a pharmaceutically acceptable salt or ester thereof.

9. A pharmaceutical composition comprising an effective antibacterial amount of bravomicin A, B, C, D, E or F, or a pharmaceutically acceptable salt or ester thereof, in combination with an inert pharmaceutically acceptable carrier or diluent.

10. The method of therapeutically treating a mammalian host affected by a bacterial infection which comprises administering to said host an effective antibacterial dose of bravomicin A, B, C, D, E or F, or a pharmaceutically acceptable salt or ester thereof.

* * * * *